United States Patent
Siddiqui et al.

(10) Patent No.: US 7,025,955 B2
(45) Date of Patent: Apr. 11, 2006

(54) METHOD FOR MAXIMIZING SCALP HEALTH AND INDUCING ENHANCED VISUAL AND TACTILE HAIR QUALITY

(75) Inventors: Mukhtar Siddiqui, San Ramon, CA (US); Yoshiaki Kawasaki, Woodstock, CT (US); Arshad H. Malik, Dublin, CA (US); Rita W. Ayer, Santa Clara, CA (US)

(73) Assignee: Shaklee Corporation, Pleasanton, CA (US)

(*) Notice: Subject to any disclaimer, the term of this patent is extended or adjusted under 35 U.S.C. 154(b) by 222 days.

(21) Appl. No.: 10/632,680

(22) Filed: Jul. 31, 2003

(65) Prior Publication Data

US 2004/0110650 A1 Jun. 10, 2004

Related U.S. Application Data

(60) Provisional application No. 60/400,200, filed on Jul. 31, 2002.

(51) Int. Cl.
*A61K 7/06* (2006.01)

(52) U.S. Cl. .................................................... 424/70.1
(58) Field of Classification Search ................ 424/70.1
See application file for complete search history.

(56) References Cited

U.S. PATENT DOCUMENTS

| | | | |
|---|---|---|---|
| 4,670,255 A | 6/1987 | Yoshizumi et al. | |
| 4,745,103 A | 5/1988 | Oono et al. | |
| 5,156,836 A | 10/1992 | Uchikawa et al. | |
| 5,215,760 A | 6/1993 | Kavoussi et al. | |
| 5,470,876 A | 11/1995 | Proctor | |
| 5,605,929 A | 2/1997 | Liao et al. | |
| 5,641,480 A | 6/1997 | Vermeer | |
| 5,674,497 A | 10/1997 | Kuwana et al. | |
| 5,702,691 A | 12/1997 | Ichinose et al. | |
| 5,710,141 A * | 1/1998 | Lin et al. | 514/162 |
| 5,747,016 A | 5/1998 | Yui et al. | |
| 5,750,107 A | 5/1998 | Nomura | |
| 5,750,108 A | 5/1998 | Edwards | |
| 5,853,728 A | 12/1998 | Tanabe et al. | |
| 5,876,703 A | 3/1999 | Ichinose et al. | |
| 5,900,239 A | 5/1999 | Mai et al. | |
| 5,972,345 A | 10/1999 | Chizick et al. | |
| 6,025,312 A | 2/2000 | Saito et al. | |
| 6,045,801 A | 4/2000 | Miyauchi et al. | |
| 6,123,934 A | 9/2000 | Koyama et al. | |
| 6,126,940 A | 10/2000 | Takahashi et al. | |
| 6,139,828 A | 10/2000 | McCullough | |
| 6,139,852 A | 10/2000 | Takeoka et al. | |
| 6,174,885 B1 | 1/2001 | Fukunishi et al. | |
| 6,177,067 B1 | 1/2001 | Magara et al. | |
| 6,190,678 B1 | 2/2001 | Hasenoehrl et al. | |
| 6,194,468 B1 | 2/2001 | Hattori et al. | |
| 6,207,694 B1 | 3/2001 | Murad | |
| 6,208,757 B1 | 3/2001 | Sinden | |
| 6,231,877 B1 | 5/2001 | Vacher et al. | |
| 6,239,164 B1 | 5/2001 | Steiner et al. | |
| 6,255,313 B1 | 7/2001 | Suzuki et al. | |
| 6,271,246 B1 | 8/2001 | Murad | |
| 6,312,675 B1 | 11/2001 | Deane | |
| 6,333,040 B1 | 12/2001 | Boyxen et al. | |
| 6,333,057 B1 | 12/2001 | Crandall | |
| 6,338,855 B1 | 1/2002 | Albacarys et al. | |
| 6,346,279 B1 | 2/2002 | Rochon | |
| 6,358,541 B1 | 3/2002 | Goodman | |
| 6,371,993 B1 | 4/2002 | Moeller et al. | |
| 6,372,234 B1 | 4/2002 | Deckers et al. | |
| 6,376,557 B1 | 4/2002 | Zaveri | |
| 6,403,110 B1 | 6/2002 | Siddiqui et al. | |
| 2002/0009472 A1 | 1/2002 | Takekoshi et al. | |
| 2003/0190337 A1 * | 10/2003 | Bissett | 424/401 |

FOREIGN PATENT DOCUMENTS

| JP | 409263531 A | 10/1997 |
|---|---|---|

* cited by examiner

*Primary Examiner*—Thurman K. Page
*Assistant Examiner*—David Vanik
(74) *Attorney, Agent, or Firm*—Klarquist Sparkman, LLP

(57) ABSTRACT

A hair care formulation is disclosed that enhances visual and/or tactile qualities of the hair. Embodiments of the formulation include a pyridoxine hydrochloride (vitamin B6), a glycyrrhizinic acid, a pantothenic acid, a pyrrolidone, an antimicrobial agent, zinc, and an antioxidant. The formulation may be included in separate hair care products, such as a shampoo, conditioner and scalp serum. In a particular embodiment, the formulation is included in a daily shampoo, a deep cleansing shampoo, a daily conditioner, a deep conditioner, and a scalp serum. In some of these examples, each of the hair care products contain at least 10 vitamins, minerals, and herbs, such as swertia extract, ginseng extract, saw palmetto extract, pyridoxine hydrochloride (vitamin $B_6$), zinc pyrrolidone carboxylic acid, superoxide dismutase, dipotassium glycyrrhizate, green tea extract, and tea tree oil.

39 Claims, No Drawings

METHOD FOR MAXIMIZING SCALP HEALTH AND INDUCING ENHANCED VISUAL AND TACTILE HAIR QUALITY

CROSS REFERENCE TO RELATED APPLICATION

This claims the benefit of U.S. Provisional Patent Application No. 60/400,200, filed Jul. 31, 2002. This provisional application is incorporated herein by reference.

FIELD OF INVENTION

The present disclosure relates to hair care products, and specifically to cosmetic hair care products intended to maximize the health of the scalp while simultaneously enhancing visual and tactile quality of the hair. Maximizing the health of the scalp helps ensure that the highest quality hair is grown, while simultaneously improving the visual and tactile quality of the hair that already exists.

BACKGROUND

Appearance of the hair has long been an important aspect of human grooming. It is, in fact, one of the first characteristics that humans notice about one another. The length, thickness, volume, color, and texture all play critical roles in the appearance of hair. Hair also affects self-esteem, which may account for the degree of attention that it receives. Persons having hair that is unmanageable, dry, oily, limp, or otherwise unconventional in appearance, regardless of the source of these problems, often seek products to address these problems. A multi-billion dollar industry has evolved to provide products that help enhance volume, shine, bounce, and manageability of hair. Such products include shampoos, conditioners, styling aids, hair sprays, hair colorants, perms, straighteners and the like.

In addition to this cosmetic market, there is a separate market for products to treat thinning hair and baldness. Although not all the products that are marketed in this segment are drug products, the predominant products are pharmaceuticals such as Rogaine® and Regaine® (topical solutions of the drug minoxidil from Upjohn, Inc.), Propecia® and Proscar® (orally ingested tablet of the drug finasteride from Merck and Company, Inc.), Andolactone® (orally ingested tablets or topical solutions of the drug sprionolactone from G. D. Searle, Inc.), Androcur® (orally ingested tablet of the drugs cyproterone acetate and ethinyl estradiol from Schering-Plough, Inc.), Eulexin® (oral tablets of the drug flutamide from Schering-Plough, Inc.). Additionally, oral contraceptives (containing estrogens and/or estradiol), tretinoin, and azelaic acid are drugs that have been the subject of scientific studies for their potential to enhance hair growth. There are also a variety of other products on the market today that claim to aid in the growth of hair.

Hair is a specialized cylindrical structure primarily composed of keratinized proteins, but it also contains a variety of other materials, such as minerals. Each hair is composed of two primary layers. The outmost layer, called the cuticle, is composed of a series of overlapping, visibly transparent platelets. These platelets are oriented in such a way that their exposed end is directed toward the distal end of the hair (the end furthest from the scalp). The cuticle completely surrounds the inner layer, which is known as the cortex. This inner layer is made of elongated strands of keratinized protein that is formed into bundles. Disulfide (—S—S—) bonds between molecules of the amino acid cysteine link both within strands and between adjacent strands. These disulfide bonds are responsible for the strength, resiliency, and curliness of hair. Some hairs have a third innermost layer, called the medulla. This layer is composed of cellular debris generated during the process of keratinization. There are no known structural attributes associated with the medulla.

Because the hair is made of protein, it can be damaged by mechanical, chemical, and thermal injury. The cuticle is often the primary focus of that damage because combing, brushing, and other forms of mechanical manipulation tend to chip off portions of the cuticle. Exposure to low relative humidities and high temperatures caused by blow dryers, curling irons, straightening irons, and hot curlers dry the cuticle such that edges of these platelets lift up. This lifting of the cuticle creates tangles between hair fibers that in turn can cause the cuticle to break, especially during mechanical manipulation. Moreover, high temperatures caused by blow dryers, curling irons, and straightening irons also can cause blisters on the cuticle platelets that leave holes or cracks in them. High pH chemicals applied to the hair cause swelling of the cuticle and concomitant opening of the spaces between cuticle platelets. If this high pH is not thoroughly neutralized following such treatments, spaces between the cuticle platelets remain open and thereby reduce the barrier properties afforded by the cuticle layer. The breakage and loss of portions of the cuticle platelets are always greatest at the most distal portions of the hair strands. Therefore, it is not unusual, especially with longer hair, to find significant loss of the cuticle layer. The loss of cuticle platelets can also result in split ends, in which the strands of the cortex fray because they are not constrained by the presence of the cuticle layer.

Hair grows from follicles in the skin that extend from the epidermis (the outmost layer of skin) to the dermis (the deepest layer of the skin). Hair growth is a complex biochemical process that is only partially understood, in part because it is extremely difficult to isolate single hair follicles and grow them in culture medium. However, it is well recognized that hair grows from active hair follicles at a rate of 0.2 to 0.5 millimeters (0.01 to 0.02 inches) per day. Hair growth is not a continuous phenomenon, but rather occurs in cycles of anagen (active growth), catagen (transition to no growth), and telogen (dormancy). A typical anagen phase lasts for 2 to 10 years, after which the cells at the base of the hair follicle enter catagen for about 14 to 21 days. At the end of the catagen phase, the follicle enters the telogen phase, and becomes dormant for a period of 30 to 90 days. During this phase, the previously growing hair detaches from the base of the follicle, and is eventually shed from the skin as it is pushed out of the follicle by the growth of new hair strand that occurs when the follicle enters a new anagen phase.

Proper hair growth depends upon maintaining the scalp in its optimal condition, by carefully keeping it nourished, conditioned, and moisturized. However, because the scalp has an abundance of sebaceous glands, it tends to be oilier than skin of many other parts of the body. Therefore, it is helpful to balance the conditioning and moisturization of the scalp with the natural oiliness of the scalp. One way to accomplish this task is through the application of a combination of vitamins, minerals, and herbs instead of (or in addition to) the application of conventional emollients and humectants.

In spite of these general teachings, there is still a need to develop specific hair care formulations and systems that balance the competing needs of the hair and scalp, and enhance the appearance of the hair.

SUMMARY

A hair care formulation is described herein that enhances visual and/or tactile qualities of the hair. The formulation includes a pyridoxine hydrochloride (vitamin B6), a glycyrrhizinic acid, a pantothenic acid, a pyrrolidone, an antimicrobial agent, zinc, and an antioxidant. In some embodiments, the formulation is included in separate hair care products, such as a shampoo and a conditioner that are individually formulated to perform their separate functions. In yet other embodiments, the formulation is included in a scalp serum treatment. In yet another example, the formulation is sold in a kit that includes a daily shampoo, a deep cleansing shampoo, a daily conditioner, a deep conditioner, and the scalp serum treatment, all of which separately include the formulation. Other kits include any subset of these products. The kit may also include instructions for using each of the shampoos, conditioners and/or scalp serum treatment. The instructions may include, for example, a precaution not to use any other shampoo or conditioner while using the present hair care system. Alternatively, or in addition, the instructions may instruct the user not to use any hair care product other than one which contains the ingredients of the disclosed hair care system.

In particular examples that are disclosed herein, the glycyrrhizinic acid comprises one or more of monoammonium glycyrrhizinate or dipotassium glycyrrhizinate; the pantothenic acid comprises panthenol; the pyrrolidone comprises pyrrolidone carboxylic acid (PCA); the antimicrobial agent comprises one or more of cajuput oil, lemongrass, lavender or tea tree oil (and in particular embodiments is tea tree oil); the zinc comprises a zinc containing compound, such as a zinc pyrrolidone, for example a zinc pyrrolidone carboxylic acid (PCA); and the antioxidant comprises one or more of a green tea extract and superoxide dismutase (SOD).

In other embodiments, the formulation further includes one or more of a blood flow stimulator (such as one or more of *zingiber officinale* root oil, *zingiber officinale* extract, or menthol), and a moisturizer.

In certain particularly disclosed examples, the formulation includes pyridoxine hydrochloride, dipotassium glycyrrhizinic acid, panthenol, zinc pyrrolidone carboxylic acid, butylene glycol, tea tree leaf oil, zinc, and green tree extract and/or superoxide dismutase.

Also disclosed is a method of enhancing the appearance and/or texture of hair, by applying the disclosed formulation to the hair in the form of, for example, a shampoo, a conditioner, and/or a scalp treatment. For example, when the formulation is included in a separate shampoo formulation and conditioner formulation, the shampoo formulation is applied to the hair in combination with water to cleanse it, and the conditioner formulation is applied to the hair to condition it. In other embodiments wherein the formulation is included in a separate shampoo formulation, deep cleansing shampoo formulation, conditioner formulation, revitalizing conditioner formulation, and scalp treatment formulation, the deep cleansing shampoo formulation is applied to the hair 1–2 times per week, and the daily shampoo is applied the other days of the week; the revitalizing conditioner formulation is applied 1–2 times per week, and the light conditioner formulation is applied to the hair the other days of the week; and the scalp treatment formulation is applied to the scalp each day of the week.

The disclosed formulation also can be used in combination with other hair care products that do not include the disclosed formulation. For example, the disclosed scalp treatment formula can be used to enhance the appearance and/or texture of hair in combination with a generic shampoo and/or conditioner.

The foregoing and other features and advantages will become more apparent from the following detailed description of several embodiments.

DETAILED DESCRIPTION OF SEVERAL EXAMPLES

The products and methods disclosed herein provide a basic formulation that is introduced into a variety of hair care products (such as shampoo, conditioner, and scalp treatment), such that the benefits provided by this formulation can be repeatedly experienced by the user. In particular embodiments, these multiple hair care products are the only shampoo, conditioner and/or scalp treatment used by the subject, such that the beneficial ingredients are not washed away by another formulation. The exclusive use of this restricted class of shampoo, conditioner and/or scalp treatment provides maximum benefit to the user. In some cases, however, other hair care products that do not contain the formulation may be used.

In certain examples, the shampoo and conditioner are sold in a kit, which optionally also includes the scalp treatment. In particular examples, the kit includes a regular shampoo designed for regular (e.g. daily or almost daily) use, a deep cleansing shampoo for use one to two times per week (instead of the regular shampoo), a light conditioner for regular (e.g. daily or almost daily use), a deep conditioner for use one to two times per week (instead of the regular conditioner), and the scalp treatment.

The shampoos include detergents for cleaning the hair, as well as fragrances, nutrients, antioxidants, surfactants, antimicrobial agents, and water as a vehicle. The shampoos are designed to remove foreign material from the hair, to expose its exterior surface and help it appear lustrous and bright. The regular shampoo is a mild cleanser that provides good foam and can be used frequently on a broad variety of hair types. In contrast, the deep cleansing shampoo is designed to gently remove the residue of styling products, mineral buildup and other environmental pollutants from a variety of hair types. The deep cleansing shampoo is designed for less frequent use than the regular shampoo. For example, the regular and deep cleansing shampoos can differ in their cleansing systems. In some cases, the daily shampoo includes less of the same surfactant/detergent than the deep cleansing shampoo, or includes additional ingredients that inhibit the cleansing action of the surfactant/detergent to make the cleanser milder, such as proteins, silicone, or herbal additives. Also, the daily shampoo can include different, milder surfactants/detergents than the deep cleansing shampoo. A milder surfactant/detergent is one that causes a lesser reduction in surface tension and less cleansing. Generally, the higher the ethoxylation of a surfactant/detergent, the milder it is, while surfactants with low ethoxylation or no ethoxylation are stronger. In one example of the regular shampoo, the cleansing ingredients include Sodium Lauryl Sulfoacetate, Disodium Laureth Sulfosuccinate, Ammonium Laureth Sulfate and Cocamidopropyl Betaine. In contrast, the deep cleansing shampoo would not use Sodium Lauryl Sulfoacetate and Disodium Laureth Sulfosuccinate that are in the daily shampoo, and Decyl Glucoside would be substituted for them. Of course, many other cleansing systems would be known to one of skill in the art for designing compositions suitable for regular cleaning or intermittent deep cleaning use.

The conditioner provides ingredients that help the hair appear noticeably smoother and softer to the touch. Typically conditioners are designed to provide detangling, static/flyaway control, easier wet and dry combing, sheen, and soft feel to the hair. Conditioners can also repair damaged hair, for example by helping mend split ends. The ingredients generally used to provide those attributes include cationic surfactants (such as quaternary ammonium compounds), proteins and their derivatives, silicones and their derivatives, long chain (high molecular weight) fatty alcohols and their derivatives, amino acids and their derivatives, vegetable oils and their derivatives, vitamins and pro vitamins, and humectants.

A light or regular conditioner is generally designed for more frequent use on a variety of hair types after shampooing. In some cases it is formulated with low actives (low solid content, for example in the range of 2 to 30%, depending upon the types of conditioning agents chosen) to avoid excessive buildup of solids on the hair. It may also have surfactants with relatively low cationic charges such that fewer solids build up on the hair. Processing or contact time is generally short, typically 1–3 minutes. In a particular disclosed example, the light conditioner contains the following conditioning ingredients: Cyclomethicone, Quaternium-82, Cetyl Alcohol, Stearyl Alcohol, Sodium Coco PG-Dimonium Chloride Phosphate, Hydrogenated Vegetable Oil, Stearamidopropyl Dimethylamine, Stearyldimonium Hydroxypropyl Hydrolyzed Wheat Protein, Wheat Amino Acids, Cinnamidopropyltrimonium Chloride, Panthenol. Whatever its composition, a light or regular conditioner is one which is intended for regular use, for example daily or almost daily use. Typically, the light conditioner is labeled with directions for regular (for example daily or almost daily) use.

Deep conditioners (revitalizing conditioners) are designed for less frequent use. They may be designed to address cumulative damage of hair. Examples of such cumulative damage include over processing with chemical treatment, use of hair appliances such as blow dryers, curling irons, and long exposure to ultraviolet radiation (e.g. the sun). Deep conditioners can include a higher solids content than light conditioners and/or include surfactants with higher cationic charges to induce greater attraction of the conditioning agent to the hair. Deep conditioners typically have a longer processing or contact time, for example 4–5 minutes or longer. Whatever its composition, a deep conditioner is intended for less than daily use, for example use 1–2 times per week. Typically the deep conditioner is labeled with directions for such infrequent use.

A specific example of a deep conditioning formulation is one that contains the following conditioning ingredients: Behentrimonium Chloride, Cetyl Alcohol, Cyclomethicone, Sodium Coco PG-Dimonium Chloride Phosphate, Wheat Germamidopropyl Dimonium Hydroxypropyl Hydrolyzed Wheat Protein, Cinnamidopropyltrimonium Chloride, Panthenol, and Wheat Amino Acids.

The scalp treatment supports scalp health by stimulating hair follicles by one or more of the following: promoting blood flow circulation, protecting the scalp and its adnexa from free radical damage, reducing inflammation, reducing the appearance of oiliness, and providing minerals and vitamins for nutrition. In particular embodiments, the scalp treatment provides all of these functions. Moreover, it can also provide either primary or adjunctive antimicrobial activity.

Examples of scalp treatment ingredients and their functions are:

Zinc and Vitamin B6—5α reductase inhibitors to control oiliness;

Swertia Extract and Ginseng Extract—Provide stimulation of blood flow;

Green Tea and Tea Tree Oil—Antimicrobials and anti-inflammatories;

Ginger—Provide tingling sensation;

Superoxide dismutase—Protection from free radicals;

Vitamins (A and E), CoQ-10, Ginseng Extract, and minerals (Copper, Zinc, Manganese,)—Provide energy, nutrition and antioxidant potential.

As used herein, "a pyridoxine" refers to the group of pyridines having Vitamin B6 activity, or any of their natural or synthetic derivatives, and includes for example: 5-hydroxy-6-methyl-3,4-pyridinedimethanol hydrochloride; pyridoxol hydrochloride; pyridoxinium chloride; adermine hydrochloride; 2-methyl-3-hydroxy-4,5-bis(hydroxymethyl)pyridine hydrochloride; Bonasanit; Hexabione hydrochloride; Hexabetalin; and others.

A "glycyrrhizinic acid" refers to that acid and its derivatives, such as monoammonium glycyrrhizinate and dipotassium glycyrrhizinate.

A "pantothenic acid" refers to a member of the vitamin B complex which is a component of coenzyme A, and may be considered a β-alanine derivative with a peptide linkage, and includes derivatives thereof, such as the alcohol form panthenol or esters such as ethyl panthenate.

A "pyrrolidone" refers to pyrrolidone and it derivatives, such as pyrrolidone carboxylic acid (PCA) and salts thereof, A "glycol polyhydric alcohol" is a dihydric polyfunctional alcohol that is physicially and chemically similar to glycerol, such as ethylene glycol, glycerin, sugars (such as glucose or sorbitol), and butylene glycol glycols, for example 1,3-butylene glycol. These materials can be used as water-soluble solvents for the extraction of botanical compounds, and in some instances (such as butylene glycol) to provide humectancy to the product.

An "antimicrobial agent" refers to any agent that has an inhibiting effect on microbes, such as bacteria, viruses and fungi. For example, the antimicrobial agent can be cajuput oil, lemongrass, lavender, or tea tree oil (and combinations thereof).

"Zinc" refers to zinc and derivatives thereof, for example zinc containing compounds, such as Zinc pyrrolidone carboxylic acid (ZnPCA). Zinc could similarly be a counterion for a variety of negatively charged species that are used in the formulation.

The source of real nourishment for the scalp, like that of the skin on any other areas of the body, comes from materials delivered to the lower skin levels by the bloodstream. Therefore, it is important to ensure that the proper blood flow is maintained to the scalp. This can be accomplished topically by a variety of materials including ingredients such as swertia extract *swertia japonica* extract), *zingiber officinale* root oil, *zingiber officinale* extract, and/or menthol. In order to ensure that these nutrients are properly converted to the energy sources needed by the scalp, ingredients such as ginseng extract (*panax ginseng* extract) and saw palmetto extract can be topically applied in combination with them.

The conditioning and moisturization of the scalp is accomplished by the topical application of vitamin $B_6$ (pryidoxine hydrochloride), dipotassium glycyrrhizate, panthenol, salts of pyrrolidone carboxylic acid (PCA), tea tree leaf oil (*melaleuca alternifolia* leaf oil), and zinc ions. Additionally, since sebum on the scalp can provide an excellent environment for the growth of undesirable microorganisms that can lead to clogged follicles and dandruff, tea tree oil can be topically applied as an antimicrobial agent. It is also helpful to protect the scalp from the damaging effects of free radicals produced by ultraviolet light and environmental pollutants. The addition of antioxidants such as green tea extract (*camellia sinensis* leaf extract) and superoxide dismutase provide this type of protection. All of these materials can be formulated into a cosmetically acceptable vehicle using commonly available ingredients known to those skilled in the art.

In order to provide the maximum possible effect involving the least amount of effort during use, it is helpful to deliver the ingredients of the formulation in every hair care product to be used by the consumer. Therefore, in specific examples, each of the ingredients of the formulation has been introduced into each of the five (5) specific products described herein. Furthermore, where appropriate, additional ingredients have been added to selected formulations in order to maximize the efficacy of the ingredients described above. Such additional ingredients can be ingredients that perform the same function as the ingredient that is being maximized (for example, adding an additional antimicrobial agent to another antimicrobial agent), or providing an agent that enhances the activity of another ingredient. For instance, ginger root oil and/or extract (*zingiber officinale* root oil and/or extract) and menthol have been added to the serum formulation in order to enhance the stimulation of the blood flow to the scalp. Vitamins A and E have been added to the serum formulation in order to enhance the conditioning and moisturizing effects of the formulation. Ethyl alcohol and galactoarabinan have also been added to boost the efficacy of the tea tree oil in this formulation. Furthermore, coenzyme Q-10 (ubiquinone) and vitamins A and E (retinyl palmitate and tocopheryl acetate, respectively) are present in an example of the formulation in order to increase the free radical scavenging efficacy of the green tea extract and superoxide dismutase.

The above ingredients have been described in terms of their effect upon the scalp. Some of these ingredients also play an important role in terms of the hair also. For instance, tea tree oil, dipotassium glycyrrhizate, PCA, and especially panthenol condition and/or moisturize the hair. The antioxidant activity of the green tea extract and superoxide dismutase provide efficient protection against free radical damage regardless of whether they are applied to the scalp or the hair. This is important since applying a product to the scalp invariably results in the application to the hair as well.

In addition to the ingredients described above, a mixture of cleansing ingredients as well as other appropriate functional ingredients (preservatives, fragrance, water, etc.) have been added to each of the shampoo formulations in such a way as to deliver the desired cleansing activity for the hair and scalp in a consumer-acceptable form. In a similar way, the ingredients described above have been added to a mixture of conditioning ingredients and other appropriate functional ingredients have been added to each of the conditioner formulations in such a way as to deliver the desired conditioning activity for the hair in a consumer-acceptable form.

A variety of formulations are disclosed herein for separate hair care products including a regular shampoo, a deep cleansing shampoo, a regular conditioner, a deep cleanser, and a scalp treatment. In particular examples, each of the separate hair care products enhance visual and/or tactile qualities of the hair and include the disclosed hair care formulation, with its ingredients listed in about the following ranges:

|  | Low % | Preferred % | High % |
| --- | --- | --- | --- |
| a pyridoxine hydrochloride | 0.00001 | 0.1 | 10 |
| a glycyrrhizinic acid; | 0.0001 | 0.05 | 12 |
| a pantothenic acid; | 0.001 | 0.125 | 20 |
| a pyrrolidone; | 0.0001 | 0.1 | 7 |
| an antimicrobial agent; | 0.0001 | 0.05 | 15 |
| zinc; and | 0.0001 | 0.1 | 10 |
| an antioxidant. | 0.00001 | 0.01 | 5 |

In particular embodiments, the formulation also includes a moisturizer.

In yet another example, the formulation includes the following ingredients, in the indicated ranges:

|  | Low % | Preferred % | High % |
| --- | --- | --- | --- |
| pyridoxine hydrochloride; | 0.00001 | 0.1 | 10 |
| dipotassium glycyrrhizinic acid; | 0.0001 | 0.05 | 12 |
| panthenol; | 0.001 | 0.125 | 20 |
| zinc pyrrolidone carboxylic acid; | 0.0001 | 0.1 | 10 |
| tea tree leaf oil; | 0.0001 | 0.05 | 15 |
| zinc; and | .0001 | 0.1 | 10 |
| green tree extract or SOD | 0.00001 | 0.1 | 5 |

In particular embodiments, the hair care formulation is included in a separate shampoo formulation and conditioner formulation. The basic hair care formulation also can be included in a separate scalp treatment formulation, which is not a shampoo formulation or conditioner formulation. In particular examples, the hair care formulation is included in a regular conditioner and deep (or revitalizing) conditioner formulation. In particular examples, the formulation is included in a separate shampoo formulation, conditioner formulation, revitalizing conditioner formulation, and scalp treatment formulation, for example wherein the set includes two shampoos and two conditioners.

In specific detailed examples, the scalp serum (scalp treatment) formulation includes the following ingredients, within about the indicated ranges.

| Ingredient | Low | Percentage by Weight (w/w) preferred | High |
| --- | --- | --- | --- |
| Water | 5.0000 | 90.2200 | 96.0000 |
| SD Alcohol 40-B | 0.1000 | 5.0000 | 75.0000 |
| Isoceteth-20 | 0.0010 | 1.5000 | 60.0000 |
| Benzyl Alcohol | 0.0001 | 0.4500 | 10.0000 |
| Water and Butylene Glycol and *Serenoa Serrulata* (Saw Palmetto) Fruit Extract | 0.0001 | 0.2500 | 25.0000 |
| Water and Butylene Glycol and Panax Ginseng Root Extract | 0.0001 | 0.2500 | 30.0000 |
| Panthenol (Liquid 50%) | 0.0010 | 0.2500 | 25.0000 |
| Water and Butylene Glycol and *Swertia Japonica* Extract | 0.0001 | 0.2500 | 25.0000 |
| Water and Butylene Glycol and *Zingiber Officinale* (Ginger) Root Extract | 0.0001 | 0.2500 | 28.0000 |
| Sodium Benzoate | 0.0010 | 0.3000 | 5.0000 |
| Methylparaben | 0.0001 | 0.2000 | 2.0000 |
| Polysorbate 80 | 0.0001 | 0.1500 | 25.0000 |
| Zinc PCA | 0.0001 | 0.1000 | 10.0000 |
| Galactoarabinan | 0.0001 | 0.1000 | 15.0000 |
| Tocopheryl Acetate | 0.0001 | 0.1000 | 10.0000 |
| Pyridoxine HCl | 0.00001 | 0.1000 | 7.0000 |
| Propylparaben | 0.0001 | 0.1000 | 2.0000 |
| Disodium EDTA | 0.0001 | 0.1000 | 5.0000 |
| Menthol | 0.00001 | 0.0500 | 20.0000 |
| *Melaleuca Alternifolia* | 0.00001 | 0.0500 | 15.0000 |

-continued

| Ingredient | Low | Percentage by Weight (w/w) preferred | High |
|---|---|---|---|
| (Tea Tree) Leaf Oil | | | |
| Dipotassium Glycyrrhizate | 0.00001 | 0.0500 | 5.0000 |
| *Camellia Sinensis* Leaf Extract | 0.00001 | 0.0500 | 28.0000 |
| Superoxide Dismutase | 0.00001 | 0.0100 | 7.0000 |
| *Zingiber Officinale* (Ginger) Root Oil | 0.00001 | 0.0500 | 15.0000 |
| Butylparaben | 0.0001 | 0.0500 | 2.0000 |

-continued

| Ingredient | Low | Percentage by Weight (w/w) preferred | High |
|---|---|---|---|
| Ubiquinone (Coenzyme Q-10) | 0.00001 | 0.0100 | 5.0000 |
| Retinyl Palmitate | 0.00001 | 0.0100 | 5.0000 |
| Total | | 100.0000 | |

In particular examples, the daily shampoo and deep cleansing shampoo formulations include the following ingredients in about the following ranges:

| Ingredient | Low | High | Percentage by Weight (w/w) Daily Shampoo | Deep Cleansing Shampoo |
|---|---|---|---|---|
| Sodium Lauryl Sulfoacetate and Disodium Laureth Sulfosuccinate | 0.10 | 75.00 | 26.00000 | — |
| Ammonium Laureth Sulfate | 0.10 | 80.00 | 21.50000 | 18.30000 |
| Water | 5.0 | 95.00 | 27.12222 | 43.83222 |
| Decyl Glucoside | 0.1 | 70.00 | — | 18.30000 |
| Cocamidopropyl Betaine | 0.1 | 75.00 | 14.50000 | 15.25000 |
| Coco-Glucoside and Glyceryl Oleate | 0.001 | 30.00 | 4.50000 | — |
| PEG-120 Methyl Glucose Dioleate | 0.01 | 25.00 | — | 2.00000 |
| Butylene Glycol | 0.01 | 20.00 | 1.75000 | — |
| Sodium Coco PG-Dimonium Chloride Phosphate | 0.001 | 20.00 | 0.50000 | 0.50000 |
| Triethanolamine 99% | 0.001 | 10.00 | 0.80000 | 0.42000 |
| Sodium Benzoate | 0.001 | 5.00 | 0.40000 | 0.40000 |
| Fragrance | 0.0001 | 10.00 | 0.40000 | 0.35000 |
| Citric Acid | 0.001 | 10.00 | — | 0.12000 |
| Capryloyl Glycine | 0.0001 | 10.000 | 0.20000 | 0.20000 |
| Undecylenoyl Glycine | 0.0001 | 10.000 | 0.10000 | 0.10000 |
| Polysorbate 80 | 0.0001 | 25.000 | 0.00722 | 0.00722 |
| Stearyldimonium Hydroxypropyl Hydrolyzed Wheat Protein | 0.0001 | 10.000 | 1.00000 | — |
| Wheat Amino Acids | 0.0001 | 10.000 | 1.00000 | — |
| Phytantriol | 0.00001 | 7.000 | 0.10000 | 0.10000 |
| Panthenol (50% liquid) | 0.001 | 25.00 | 0.10000 | 0.10000 |
| Water and Butylene Glycol and *Swertia Japonica* Extract | 0.00001 | 10.0000 | 0.00722 | 0.00722 |
| Butylene Glycol and *Panax Ginseng* Root Extract | 0.00001 | 10.0000 | 0.00361 | 0.00361 |
| Butylene Glycol and *Serenoa Serrulata* Extract | 0.00001 | 10.0000 | 0.00361 | 0.00361 |
| Pyridoxine Hydrochloride (Vitamin B6) | 0.00001 | 10.0000 | 0.00144 | 0.00144 |
| Zinc PCA | 0.00001 | 8.0000 | 0.00144 | 0.00144 |
| Superoxide Dismutase | 0.00001 | 8.0000 | 0.00108 | 0.00108 |
| *Camellia Sinensis* Leaf Extract (Green Tea Extract) | 0.00001 | 10.0000 | 0.00072 | 0.00072 |
| Dipotassium Glycyrrhizate | 0.00001 | 8.0000 | 0.00072 | 0.00072 |
| *Melaleuca Alternifolia* (Tea Tree) Leaf Oil | 0.00001 | 10.0000 | 0.00072 | 0.00072 |
| Total | | | 100.00000 | 100.00000 |

In another specific example, the light conditioner and revitalizing conditioner formulations include the following ingredients in the following ranges:

| Ingredient | Low | High | Percentage by Weight (w/w) preferred Light Conditioner | Revitalizing Conditioner |
|---|---|---|---|---|
| Water | 5.00 | 97.00 | 79.77222 | 76.24222 |
| Glyceryl Stearate (and) PEG-100 Stearate | 0.01 | 15.00 | 3.50000 | 1.5 |
| C14–22 Alkylalcohol and C12–20 Alkylglucoside | 0.01 | 20.00 | 2.50000 | 3.00000 |

-continued

| Ingredient | Low | High | Light Conditioner | Revitalizing Conditioner |
|---|---|---|---|---|
| Behentrimonium Chloride | 0.01 | 15.00 | — | 2.50000 |
| Cyclomethicone | 0.001 | 25.00 | 2.00000 | 1.50000 |
| Quaternium-82 | 0.0001 | 25.00 | 2.00000 | — |
| Cetyl Alcohol | 0.001 | 15.00 | 1.50000 | 2.50000 |
| Wheat Germamidopropyl Dimonium Hydroxypropyl Hydrolyzed Wheat Protein | 0.0001 | 20.000 | — | 3.00000 |
| Trilaureth-4 Phosphate | 0.001 | 15.00 | — | 1.50000 |
| Stearyl Alcohol | 0.001 | 15.00 | 1.20000 | 1.00000 |
| Glyceryl Stearate | 0.001 | 15.00 | 1.00000 | — |
| Benzyl Alcohol | 0.0001 | 10.00 | 0.95000 | 0.95000 |
| Hydroxyethylcellulose | 0.0001 | 10.00 | 0.75000 | 1.00000 |
| Sodium Coco PG-Dimonium Chloride Phosphate | 0.001 | 20.00 | 0.50000 | 0.50000 |
| Citric Acid | 0.001 | 5.00 | 0.45000 | 0.28000 |
| Fragrance | 0.0001 | 10.00 | 0.40000 | 0.40000 |
| Stearamidopropyl Dimethylamine | 0.0001 | 25.00 | 0.40000 | 0.50000 |
| Hydrogenated Vegetable Oil | 0.001 | 15.00 | 0.25000 | — |
| Phenyl Trimethicone | 0.001 | 30.00 | 0.25000 | — |
| Methylparaben | 0.0001 | 2.00 | 0.20000 | 0.20000 |
| Sodium Benzoate | 0.001 | 5.00 | 0.20000 | 0.20000 |
| Disodium EDTA | 0.001 | 5.00 | 0.10000 | 0.10000 |
| Propylparaben | 0.001 | 2.00 | 0.10000 | 0.10000 |
| Butylparaben | 0.001 | 2.00 | 0.05000 | 0.05000 |
| Polysorbate 80 | 0.0001 | 25.00 | 0.00722 | 0.00722 |
| Stearyldimonium Hydroxypropyl Hydrolyzed Wheat Protein | 0.0001 | 15.00 | 0.50000 | — |
| Wheat Amino Acids | 0.0001 | 10.00 | 0.50000 | 1.00000 |
| Cinnamidopropyltrimonium Chloride | 0.0001 | 15.00 | 0.50000 | 0.50000 |
| Phytantriol | 0.0001 | 10.00 | 0.10000 | 0.10000 |
| Panthenol (50% Liquid) | 0.001 | 25.00 | 0.10000 | — |
| Galactoarabinan | 0.0001 | 15.00 | 0.20000 | 0.20000 |
| Sodium Cocoyl Amino Acids and Potassium Dimethyl Copolyol Panthenyl Phosphate | 0.00001 | 6.00 | — | 0.10000 |
| Butylene Glycol and *Helianthus Annuus* (Sunflower) Seed Extract | 0.00001 | 15.00 | — | 0.05000 |
| Water and Butylene Glycol and *Swertia Japonica* Extract | 0.00001 | 10.0000 | 0.00722 | 0.00722 |
| Butylene Glycol and Panax Ginseng Root Extract | 0.00001 | 10.0000 | 0.00361 | 0.00361 |
| Butylene Glycol and *Serenoa Serrulata* Extract | 0.00001 | 10.0000 | 0.00361 | 0.00361 |
| Pyridoxine Hydrochloride (Vitamin B6) | 0.00001 | 10.0000 | 0.00144 | 0.00144 |
| Zinc PCA | 0.00001 | 8.0000 | 0.00144 | 0.00144 |
| Superoxide Dismutase | 0.00001 | 8.0000 | 0.00108 | 0.00108 |
| *Camellia Sinensis* Leaf Extract (Green Tea Extract) | 0.00001 | 10.0000 | 0.00072 | 0.00072 |
| Dipotassium Glycyrrhizate | 0.00001 | 8.0000 | 0.00072 | 0.00072 |
| *Melaleuca Alternifolia* (Tea Tree) Leaf Oil | 0.00001 | 10.0000 | 0.00072 | 0.00072 |
| Total | | | 100.00000 | 100.00000 |

To help better illustrate these concepts, the compositions of examples of five formulations are shown in Examples 1 through 5. The use of some of the ingredients contained in these examples has been described in the patent literature for promotion of hair growth and/or for the treatment of thinning hair. However, the formulation (and the method of using it) is directed at maximizing the condition of the scalp while simultaneously increasing the visual and/or tactile qualities of the hair. Therefore, the combinations of the ingredients employed in the specific examples cannot be considered as having been described by that prior art.

Example 1 provides the specific composition of a scalp serum containing each of the ingredients described previously.

Examples 2 and 3 provide the specific compositions of the two shampoo formulations previously described in more general terms.

Examples 4 and 5 provide the specific compositions of the two conditioner formulations previously described in more general terms.

EXAMPLE 1
Scalp Serum

| Ingredient | Percentage by Weight (w/w) |
|---|---|
| Water | 90.2200 |
| SD Alcohol 40-B | 5.0000 |
| Isoceteth-20 | 1.5000 |
| Benzyl Alcohol | 0.4500 |
| Water and Butylene Glycol and *Serenoa Serrulata* Fruit Extract | 0.2500 |
| Water and Butylene Glycol and Panax Ginseng Root Extract | 0.2500 |
| Panthenol (Liquid 50%) | 0.2500 |
| Water and Butylene Glycol and *Swertia Japonica* Extract | 0.2500 |
| Water and Butylene Glycol and *Zingiber Officinale* (Ginger) Root Extract | 0.2500 |
| Sodium Benzoate | 0.3000 |
| Methylparaben | 0.2000 |
| Polysorbate 80 | 0.1500 |
| Zinc PCA | 0.1000 |

-continued

| Ingredient | Percentage by Weight (w/w) |
|---|---|
| Galactoarabinan | 0.1000 |
| Tocopheryl Acetate | 0.1000 |
| Pyridoxine HCl | 0.1000 |
| Propylparaben | 0.1000 |
| Disodium EDTA | 0.1000 |
| Menthol | 0.0500 |
| *Melaleuca Alternifolia* (Tea Tree) Leaf Oil | 0.0500 |
| Dipotassium Glycyrrhizate | 0.0500 |
| *Camellia Sinensis* Leaf Extract | 0.0500 |
| Superoxide Dismutase | 0.0100 |
| *Zingiber Officinale* (Ginger) Root Oil | 0.0500 |
| Butylparaben | 0.0500 |
| Ubiquinone (Coenzyme Q-10) | 0.0100 |
| Retinyl Palmitate | 0.0100 |
| Total | 100.0000 |

EXAMPLE 2

Daily Shampoo

| Ingredient | Percentage by Weight (w/w) |
|---|---|
| Sodium Lauryl Sulfoacetate and Disodium Laureth Sulfosuccinate | 26.00000 |
| Ammonium Laureth Sulfate | 21.50000 |
| Water | 27.12222 |
| Cocamidopropyl Betaine | 14.50000 |
| Coco-Glucoside and Glyceryl Oleate | 4.50000 |
| Butylene Glycol | 1.75000 |
| Sodium Coco PG-Dimonium Chloride Phosphate | 0.50000 |
| Triethanolamine 99% | 0.80000 |
| Sodium Benzoate | 0.40000 |
| Fragrance | 0.40000 |
| Capryloyl Glycine | 0.20000 |
| Undecylenoyl Glycine | 0.10000 |
| Polysorbate 80 | 0.00722 |
| Stearyldimonium Hydroxypropyl Hydrolyzed Wheat Protein | 1.00000 |
| Wheat Amino Acids | 1.00000 |
| Phytantriol | 0.10000 |
| Panthenol (50% liquid) | 0.10000 |
| Water and Butylene Glycol and *Swertia Japonica* Extract | 0.00722 |
| Butylene Glycol and Panax Ginseng Root Extract | 0.00361 |
| Butylene Glycol and *Serenoa Serrulata* Extract | 0.00361 |
| Pyridoxine Hydrochloride (Vitamin B6) | 0.00144 |
| Zinc PCA | 0.00144 |
| Superoxide Dismutase | 0.00108 |
| *Camellia Sinensis* Leaf Extract (Green Tea Extract) | 0.00072 |
| Dipotassium Glycyrrhizate | 0.00072 |
| *Melaleuca Alternifolia* (Tea Tree) Leaf Oil | 0.00072 |
| Total | 100.00000 |

EXAMPLE 3

Deep Cleansing Shampoo

| Ingredient | Percentage by Weight (w/w) |
|---|---|
| Water | 43.83222 |
| Decyl Glucoside | 18.30000 |
| Ammonium Laureth Sulfate | 18.30000 |
| Cocamidopropyl Betaine | 15.25000 |
| PEG-120 Methyl Glucose Dioleate | 2.00000 |
| Sodium Coco PG-Dimonium Chloride Phosphate | 0.50000 |
| Triethanolamine 99% | 0.42000 |
| Sodium Benzoate | 0.40000 |
| Fragrance | 0.35000 |
| Citric Acid | 0.12000 |
| Capryloyl Glycine | 0.20000 |
| Undecylenoyl Glycine | 0.10000 |
| Polysorbate 80 | 0.00722 |
| Phytantriol | 0.10000 |
| Panthenol (50% Liquid) | 0.10000 |
| Water and Butylene Glycol and *Swertia Japonica* Extract | 0.00722 |
| Butylene Glycol and Panax Ginseng Root Extract | 0.00361 |
| Butylene Glycol and *Serenoa Serrulata* Extract | 0.00361 |
| Pyridoxine Hydrochloride (Vitamin B6) | 0.00144 |
| Zinc PCA | 0.00144 |
| Superoxide Dismutase | 0.00108 |
| *Camellia Sinensis* Leaf Extract (Green Tea Extract) | 0.00072 |
| Dipotassium Glycyrrhizate | 0.00072 |
| *Melaleuca Alternifolia* (Tea Tree) Leaf Oil | 0.00072 |
| Total | 100.00000 |

EXAMPLE 4

Light Conditioner

| Ingredient | Percentage by Weight (w/w) |
|---|---|
| Water | 79.77222 |
| Glyceryl Stearate (and) PEG-100 Stearate | 3.50000 |
| C14–22 Alkylalcohol and C12–20 Alkylglucoside | 2.50000 |
| Cyclomethicone | 2.00000 |
| Quaternium-82 | 2.00000 |
| Cetyl Alcohol | 1.50000 |
| Stearyl Alcohol | 1.20000 |
| Glyceryl Stearate | 1.00000 |
| Benzyl Alcohol | 0.95000 |
| Hydroxyethylcellulose | 0.75000 |
| Sodium Coco PG-Dimonium Chloride Phosphate | 0.50000 |
| Citric Acid | 0.45000 |
| Fragrance | 0.40000 |
| Stearamidopropyl Dimethylamine | 0.40000 |
| Hydrogenated Vegetable Oil | 0.25000 |
| Phenyl Trimethicone | 0.25000 |
| Methylparaben | 0.20000 |
| Sodium Benzoate | 0.20000 |
| Disodium EDTA | 0.10000 |
| Propylparaben | 0.10000 |
| Butylparaben | 0.05000 |
| Polysorbate 80 | 0.00722 |
| Stearyldimonium Hydroxypropyl Hydrolyzed Wheat Protein | 0.50000 |
| Wheat Amino Acids | 0.50000 |
| Cinnamidopropyltrimonium Chloride | 0.50000 |
| Phytantriol | 0.10000 |
| Panthenol (50% Liquid) | 0.10000 |
| Galactoarabinan | 0.20000 |
| Water and Butylene Glycol and *Swertia Japonica* Extract | 0.00722 |
| Butylene Glycol and Panax Ginseng Root Extract | 0.00361 |
| Butylene Glycol and *Serenoa Serrulata* Extract | 0.00361 |
| Pyridoxine Hydrochloride (Vitamin B6) | 0.00144 |
| Zinc PCA | 0.00144 |

-continued

| Ingredient | Percentage by Weight (w/w) |
|---|---|
| Superoxide Dismutase | 0.00108 |
| Camellia Sinensis Leaf Extract (Green Tea Extract) | 0.00072 |
| Dipotassium Glycyrrhizate | 0.00072 |
| Melaleuca Alternifolia (Tea Tree) Leaf Oil | 0.00072 |
| Total | 100.00000 |

EXAMPLE 5

Revitalizing Conditioner

| Ingredient | Percentage by Weight (w/w) |
|---|---|
| Water | 76.24222 |
| C14–22 Alkylalcohol and C12–20 Alkylglucoside | 3.00000 |
| Behentrimonium Chloride | 2.50000 |
| Cetyl Alcohol | 2.50000 |
| Glyceryl Stearate and PEG-100 Stearate | 1.50000 |
| Cyclomethicone | 1.50000 |
| Trilaureth-4 Phosphate | 1.50000 |
| Glyceryl Monostearate | 1.00000 |
| Hydroxyethycellulose | 1.00000 |
| Benzyl Alcohol | 0.95000 |
| Sodium Coco PG-Dimonium Chloride Phosphate | 0.50000 |
| Stearamidopropyl Dimethylamine | 0.50000 |
| Fragrance | 0.40000 |
| Citric Acid | 0.28000 |
| Methylparaben | 0.20000 |
| Sodium Benzoate | 0.20000 |
| Disodium EDTA | 0.10000 |
| Propylparaben | 0.10000 |
| Butylparaben | 0.05000 |
| Polysorbate 80 | 0.00722 |
| Wheat Germamidopropyl Dimonium Hydroxypropyl Hydrolyzed Wheat Protein | 3.00000 |
| Panthenol | 1.00000 |
| Wheat Amino Acids | 1.00000 |
| Cinnamidopropyltrimonium Chloride | 0.50000 |
| Galactoarabinan | 0.20000 |
| Phytantriol | 0.10000 |
| Sodium Cocoyl Amino Acids and Potassium Dimethicone Copolyol Panthenyl Phosphate | 0.10000 |
| Butylene Glycol and Helianthus (Sunflower) Annuus Seed Extract | 0.05000 |
| Water and Butylene Glycol and Swertia Japonica Extract | 0.00722 |
| Butylene Glycol and Panax Ginseng Root Extract | 0.00361 |
| Butylene Glycol and Serenoa Serrulata Extract | 0.00361 |
| Pyridoxine Hydrochloride (Vitamin B6) | 0.00144 |
| Zinc PCA | 0.00144 |
| Superoxide Dismutase | 0.00108 |
| Camellia Sinensis Leaf Extract (Green Tea Extract) | 0.00072 |
| Dipotassium Glycyrrhizate | 0.00072 |
| Melaleuca Alternifolia (Tea Tree) Leaf Oil | 0.00072 |
| Total | 100.00000 |

EXAMPLE 6

Clinical Test Results

A human use study was conducted with the formulations described in Examples 1 through 5. The aim of this study was to evaluate the ability of these formulations to improve the condition of the hair and scalp through the use of a combination of objective and subjective methods. Thirty (30) subjects were enrolled in the study—fifteen (15) subjects with normal-to-oily hair and fifteen (15) subjects with normal-to-dry hair. The segmentation of subjects into these two categories was based upon a visual and textural evaluation of the hair and scalp by a trained expert as well as on information obtained from the subjects themselves. This test population was composed of 27 females and 3 males between the ages of 25 and 55 years of age. Their hair was a minimum of 2 inches in length for men and 4.5 inches for females. Additionally, these subjects were chosen because they reported to have experienced 1) minor to moderate hair loss, 2) thin to normal hair bulk density, 3) no prior use of severe chemical processing (i.e., double process bleaching), 4) the absence of scalp diseases, and 5) no prior use of topical or oral medication for hair loss. All subjects agreed to use only the test products issued to them on a daily basis as instructed during the entire test period.

Once enrolled, each subject was given a commercially available shampoo and instructed to use only this product to cleanse their hair at least once per day for a period of 7 days irrespective of the condition of their hair. They were instructed not to use any other hair care product during this washout period, including conditioners, styling gels, hair sprays, etc. At the end of this washout period, the test subjects were ready to begin the test involving the formulations described in Examples 1 through 5. On the night before reporting to the laboratory for the initial objective evaluation of the condition of their hair and scalp (the Day 0 evaluation), the test subjects were instructed to wash the hair with the issued shampoo and to dry it by patting the hair gently with a towel. They were further instructed not to blow dry or comb their hair.

The subjects reported to the testing laboratory for the initial evaluation (Day 0). They were seated in a room kept at a standard temperature and humidity for approximately 30 minutes. This was to acclimatize their hair to these conditions. Following acclimatization, the test subjects were seated in a comfortable chair and covered with a plastic drape. Their hair was then combed twice in a regimented manner so that all hair removed was captured. The first combing was conducted by passing a broad-toothed hard rubber comb through the subject's hair a minimum number of times in order to cover the entire head. This combing was employed to detangle the hair. All of the hair removed from the head by this initial combing was collected, placed into a container appropriately marked to indicate the source and date of the sample, and then set aside. Then the hair was combed again. This combing was conducted by passing a narrow-toothed hard rubber comb through the subject's hair no less than 20 times (but for the same number of times at each subsequent visit) in a standardized pattern covering the entire head. All of the hair removed from the head by this second combing was collected, placed into a container appropriately marked to indicate the source and date of the sample and set aside.

The weight of hair comprising the second collection of hair (obtained from combing the hair with the narrow-toothed comb) was accurately measured on an analytical balance. Each hair in this sample was then microscopically examined and separated into hairs that exhibited breakage and hairs that exhibited hair bulbs. The number of hairs comprising each of the groups was accurately counted. Additionally, the composite of all hairs exhibiting hair bulbs was also accurately weighted using the analytical balance.

In addition to this collection of hair, a standard number of hairs were plucked from parietal or occipital region of the head of a randomly selected sub-group of test subjects. These hairs were employed to microscopically measure the diameter of the hair.

Each test subject was then given a bottle of each of the five (5) formulations shown in Examples 1 through 5 above along with appropriate instructions for their use. Subjects with normal-to-oily hair were instructed to use Deep Cleansing Shampoo (shown in Example 3) twice per week, the Revitalizing Conditioner (shown in Example 5) once a week, and the Daily Shampoo (shown in Example 2) along with the Light Conditioner (shown in Example 4) on each of the remaining days of the week. They were also instructed to apply the Scalp Treatment (shown in Example 1) every day. Subjects with normal-to-dry hair were instructed to use the Deep Cleansing Shampoo (shown in Example 3) once a week, the Revitalizing Conditioner (shown in Example 5) twice a week and the Daily Shampoo (shown in Example 2) along with the Light Conditioner (shown in Example 4) on each of the remaining days of the week. This group was also instructed to apply the Scalp Treatment (shown in Example 1) every day.

Test subjects used the five test formulations for a total period of ninety (90) days. At the end of 30, 60, and 90 days of use of the test formulations according to the regimen described above, the test subjects returned to the testing laboratory for a complete evaluation of their hair according to the procedure described above.

A questionnaire was administered to each subject at each visit. These questionnaires captured their perceptions about the condition of the hair and scalp from a consumer's point of view. The questionnaire employed a five point evaluation scale in which an improvement of the attribute being evaluated is represented by a higher rating value and a decline represented by a lower rating value.

A statistical evaluation was conducted on each objective and subjective parameter in comparison to baseline (Day 0) values. Objective parameters were considered statistically significant if they were different from baseline values at the 95% confidence level using a matched-pairs comparison student t-test. The subjective ratings were considered statistically significant if they were different from baseline values at the 90% confidence level, or greater using the Mann-Whitney U-test for non-parametric parameters.

The results of this test procedure are shown in Tables 1 and 2. These results clearly demonstrate that the use of these formulations maximize the condition of the scalp while simultaneously increasing the visual and tactile properties of the hair.

The objective results demonstrating that the condition of the scalp is optimized are found in the total number of hairs lost as well as in the number and weight of bulbous hairs lost as shown in Table 1. This data clearly demonstrates that the scalp condition has been optimized since the total number of hairs lost is reduced. In fact, the data is statistically significantly at 60 and 90 days for all subjects participating in this test as well as at 60 and 90 days for the normal-to-oily test subjects and at 90 days for the normal-to-dry test subjects. If the condition of the scalp had not been improved, this value would not have declined as rapidly or significantly as it did since the condition of the scalp determines the rate at which hair is lost. Similar results are found for number and weight of bulbous hairs lost during this test, although the statistical significance found for this parameter is not as definitive as those for the total number of hairs lost. However, the same trend is found in the reduction in the numbers and weight of bulbous hairs lost as for total hairs lost. Since bulbous hairs represent hairs that were growing at the time that they were removed by combing, their loss represents hairs that were lost because the condition of the scalp was not conducive to the retention of these growing hairs. A reduction in the number of bulbous hairs lost therefore clearly indicates an improvement in the condition of the scalp since growing hair (i.e., hairs with hair bulbs) should not be lost.

The subjective data demonstrating the optimization of the condition of the scalp are found in the results from the questions pertaining to the hair loss observed in the sink and the hair loss observed when dry combing as shown in Table 2. This data demonstrates that, as a composite group, the test subjects perceived statistically less hair in their sinks and less hair loss during combing at 30, 60, and 90 days of use of the test formulas compared to that experienced at the start of the test. As was explained for the results of the objective measures, these results can only be interpreted as an improvement in the condition of the scalp. The fact that the ratings improved with time adds further support to this conclusion.

The objective results demonstrating an induced increase in the visual and tactile quality of the hair are found in the number of broken hairs lost and the percentage difference in the diameter of the hair as shown in Table 1. The number of broken hairs lost decreased across all subject categories throughout the testing period. In fact, the result for all subjects was statistically significant at 30, 60, and 90 days. This same statistical significance was found for the subjects with normal-to-oily hair. No such statistical significant difference was found for subjects with normal-to-dry hair although the results clearly demonstrate an improvement in this measure of efficacy (a 53 and 59% improvement at 60 and 90 days, respectively). However, because dry hair tends to be the most susceptible to breakage because of the brittleness of the hair, it should not be surprising that a lack of statistical difference would be found for this group of subjects. Since hair breakage is a result of the quality of the hair, and since a reduction in the amount of hair that is broken was found, these results can only be interpreted as an improvement in the quality of the hair through the use of the test formulations.

The percent difference in hair diameter increased during the test period. This increase was statistically significant at both 60 and 90 days when assessed for all subjects. This increase in hair diameter was in the range of 8 to 12% for subjects with normal-to-oily hair. The range for subjects with normal-to-dry hair was only 2 to 3%. On average across all subjects the range was 6 to 9%. These results are in line with expectations since it is difficult to significantly increase the diameter of the hair in only a 90-day test period. However, given that fact, the results obtained definitely demonstrate that the diameter of the hair has been increased. Therefore, the visual and tactile quality of the hair is improved as measured by this increase in hair diameter.

The subjective data demonstrating an induced increase in the visual and tactile quality of the hair are found in the results for the assessments of hair breakage during both wet and dry combing, ease of combing when the hair is either wet or dry, hair manageability, hair thickness, hair volume, hair body, and hair shine as shown in Table 2. Virtually every one of these parameters was found to be statistically significantly improved by the test subjects during the 90-day test period. Most of these parameters were found to be statistically different from baseline ratings at multiple time points during the test. Furthermore, the ratings for each of the parameters increased throughout the testing period. Since each of these parameters relates directly to the visual and tactile qualities of the hair (hair breakage when combing, ease of combing, manageability, thickness, volume, body and shine), it is obvious that the use of the test products induced an increase in the visual and textural properties of the hair.

The results of this test clearly demonstrate that the use of the five (5) formulations of Examples 1–5 optimize scalp health and induce increased visual and tactile hair quality.

and scalp as measured by a combination of objective and subjective methods. Thirty (30) subjects were enrolled in the study—eighteen (18) females and twelve (12) males all between the ages of 25 and 55 years of age. Their hair was a minimum of 2 inches in length for men and 4.5 inches for females. Additionally, these subjects were chosen because they reported to have experienced 1) minor to moderate hair loss, 2) thin to normal hair bulk density, 3) no severe chemical processing of the hair, as confirmed by a trained laboratory technician (i.e., double process bleaching), 4) the absence of scalp diseases, and 5) no prior use of topical or oral medication for hair loss. All subjects agreed to use only

TABLE 1

Objective Results of Human Test [a]

| Parameter Evaluated | All Subjects | | | | Normal-to-Oily Subjects | | | | Normal-to-Dry Subjects | | | |
|---|---|---|---|---|---|---|---|---|---|---|---|---|
| | 0 | 30 | 60 | 90 | 0 | 30 | 60 | 90 | 0 | 30 | 60 | 90 |
| Total Weight of Hair Lost (grams) | 0.063 | 0.056 | 0.029 | 0.022 | 0.072 | 0.067 | 0.030 | 0.026 | 0.054 | 0.046 | 0.027 | 0.018 |
| Percent Reduction in Total Hair Lost | — | 11 | 54 | 65 | — | 7 | 58 | 63 | — | 15 | 50 | 67 |
| Number of Broken Hairs Lost | 110 | 69 | 43 | 30 | 133 | 78 | 45 | 25 | 86 | 61 | 41 | 35 |
| Percent Reduction in Number of Broken Hairs Lost | — | 37 | 61 | 73 | — | 42 | 67 | 81 | — | 30 | 53 | 59 |
| Number of Bulbous Hairs Lost | 50 | 42 | 29 | 23 | 61 | 47 | 27 | 21 | 39 | 36 | 32 | 24 |
| Percent Reduction in Number of Bulbous Hairs Lost | — | 17 | 42 | 55 | — | 23 | 56 | 66 | — | 7 | 18 | 38 |
| Weight of Bulbous Hairs Lost (grams) | 0.045 | 0.052 | 0.021 | 0.018 | 0.048 | 0.064 | 0.020 | 0.022 | 0.042 | 0.039 | 0.022 | 0.015 |
| Percent Reduction in Weight of Bulbous Hairs Lost | — | −16 | 53 | 59 | — | −33 | 58 | 55 | — | 7 | 48 | 64 |
| Percent Difference in Hair Diameter | | −2 | 9 | 6 | — | 2 | 12 | 8 | — | −10 | 3 | 2 |

[a] Values listed in bold were found to be statistically significantly different from initial (Day 0) values at the 95% confidence level when evaluated using a matched pairs statistical comparison.

TABLE 2

Results of Subjective Evaluations (Average Rating Value)[a]

| Parameter Evaluated | All Subjects | | | | Normal-to-Oily Subjects | | | | Normal-to-Dry Subjects | | | |
|---|---|---|---|---|---|---|---|---|---|---|---|---|
| | 0 | 30 | 60 | 90 | 0 | 30 | 60 | 90 | 0 | 30 | 60 | 90 |
| Hair Loss Observed in Sink | 2.76 | 3.15 | 3.09 | 3.39 | 2.77 | 3.18 | 3.12 | 3.18 | 2.75 | 3.13 | 3.06 | 3.63 |
| Hair Loss When Dry Combing | 2.91 | 3.30 | 3.33 | 3.33 | 3.00 | 3.29 | 3.24 | 3.24 | 2.81 | 3.31 | 3.44 | 3.44 |
| Hair Breakage When Dry Combing | 3.15 | 3.58 | 3.52 | 3.61 | 3.12 | 3.47 | 3.35 | 3.65 | 3.19 | 3.69 | 3.69 | 3.56 |
| Hair Breakage When Wet Combing | 2.88 | 3.21 | 3.33 | 3.58 | 2.94 | 3.00 | 3.24 | 3.53 | 2.81 | 3.44 | 3.44 | 3.63 |
| Ease of Combing When Dry | 3.24 | 3.48 | 3.36 | 3.58 | 3.18 | 3.41 | 3.18 | 3.47 | 3.31 | 3.56 | 3.56 | 3.69 |
| Ease of Combing When Wet | 2.82 | 3.30 | 3.42 | 3.61 | 2.71 | 3.18 | 3.12 | 3.35 | 2.94 | 3.44 | 3.75 | 3.88 |
| Hair Manageability When Dry | 2.82 | 3.06 | 3.15 | 3.42 | 2.65 | 3.12 | 3.29 | 3.35 | 3.00 | 3.00 | 3.00 | 3.50 |
| Hair Thickness When Dry | 2.15 | 2.58 | 2.61 | 2.88 | 2.06 | 2.29 | 2.29 | 2.53 | 2.25 | 2.88 | 2.94 | 3.25 |
| Hair Volume When Dry | 2.36 | 2.70 | 2.79 | 2.94 | 2.00 | 2.47 | 2.47 | 2.53 | 2.75 | 2.94 | 3.13 | 3.38 |
| Hair Body When Dry | 2.27 | 2.52 | 2.67 | 2.94 | 1.94 | 2.47 | 2.41 | 2.65 | 2.63 | 2.56 | 2.94 | 3.25 |
| Hair Shine When Dry | 3.06 | 3.12 | 3.39 | 3.55 | 3.00 | 3.24 | 3.47 | 3.59 | 3.13 | 3.00 | 3.31 | 3.50 |

[a] Values listed in bold were found to be statistically significantly different from initial (Day 0) values at the 90% confidence level or greater when evaluated using the Mann-Whiney U-Test for non-parametric comparisons.

EXAMPLE 7

Clinical Test Results

A human use study was conducted to determine the effect of using the scalp treatment formulation described in Example 1 with generic shampoo and conditioner rather than other hair care products also including the disclosed hair care formulation. This study demonstrates the ability of the scalp treatment alone to improve the condition of the hair the test products issued to them on a daily basis as instructed during the entire test period.

Once enrolled the subjects were randomly assigned in even numbers to one of two groups, either the Nourishing Scalp Treatment Group (which used the scalp treatment), or the Placebo Group (which used a placebo rather than the scalp treatment). Each subject was given a generic, commercially available shampoo and instructed to use only this product to cleanse their hair at least once per day for a period of 7 days irrespective of the condition of their hair. They were instructed not to use any other hair care product during this washout period, including conditioners, styling gels, hair sprays, etc. At the end of this washout period, the test subjects were ready to begin the test involving the formulation described in Example 1. On the night before reporting to the laboratory for the initial objective evaluation of the condition of their hair and scalp (the Day 0 evaluation), the test subjects were instructed to wash the hair with the issued generic shampoo and to dry it by patting the hair gently with a towel. They were further instructed not to blow dry or comb their hair.

The subjects reported to the testing laboratory for the initial evaluation (Day 0). They were seated in a room kept at a standard temperature and humidity for approximately 30 minutes. This was to acclimatize their hair to these conditions. Following acclimatization, the test subjects were seated in a comfortable chair and covered with a plastic drape. Their hair was then combed twice in a regimented manner so that all hair removed was captured. The first combing was conducted by passing a broad-toothed hard rubber comb through the subject's hair a minimum number of times in order to cover the entire head. This combing was employed to detangle the hair. All of the hair removed from the head by this initial combing was collected, placed into a container appropriately marked to indicate the source and date of the sample, and then set aside. Then the hair was combed again. This combing was conducted by passing a narrow-toothed hard rubber comb through the subject's hair no less than 20 times (but for the same number of times at each subsequent visit) in a standardized pattern covering the entire head. All of the hair removed from the head by this second combing was collected, placed into a container appropriately marked to indicate the source and date of the sample and set aside.

The weight of hair comprising the second collection of hair (obtained from combing the hair with the narrow-toothed comb) was accurately measured on an analytical balance. Each hair in this sample was then microscopically examined and separated into hairs that exhibited breakage and hairs that exhibited hair bulbs. The number of hairs comprising each of the groups was accurately counted. Additionally, the composite of all hairs exhibiting hair bulbs was also accurately weighed using the analytical balance.

In addition to this collection of hair, 10 hairs were plucked from parietal or occipital region of the head of a randomly selected sub-group of each group of test subjects. These hairs were examined microscopically to measure the diameter of the hair and to determine the number of hairs in the anagen or telogen phase.

A questionnaire was administered to each subject. These questionnaires captured the subject's perceptions about the condition of the hair and scalp. The questionnaire employed a five point evaluation scale in which an improvement of the attribute being evaluated was represented by a higher rating value and a decline represented by a lower rating value.

Each test subject was then given a bottle the scalp serum (Nourishing Scalp Treatment) formulation shown in Example 1 or a placebo (90% water and 10% alcohol (w/w %)) along with a generic shampoo and conditioner. The test subjects were instructed to use the shampoo and conditioner daily and to apply the Nourishing Scalp Treatment or placebo every day. Test subjects followed this regimen for a total period of ninety (90) days. At the end of 45 and 90 days the test subjects returned to the testing laboratory for a complete evaluation of their hair according to the procedure described above, except that no questionnaires were completed at the 45-day evaluation.

A statistical evaluation was conducted for each objective and subjective parameter in comparison to baseline (Day 0) values. Objective parameters were considered statistically significant if they were different from baseline values at the 95% confidence level using a matched-pairs comparison student t-test. The subjective ratings were considered statistically significant if they were different from baseline values at the 90% confidence level or greater using the Mann-Whitney U-test for non-parametric parameters.

The results of this test procedure are shown in Tables 3–5. These results clearly demonstrate that the use of the Nourishing Scalp Treatment, even in the absence of other formulations used in Example 6 and only with generic shampoo and conditioner, maximizes the condition of the scalp while simultaneously increasing the visual and tactile properties of the hair.

The Nourishing Scalp Treatment caused a statistically significant increase in the anagen to telogen ratio, which was statistically significantly greater than the increase observed with the placebo. This is a key indicator of scalp health. Also, although not as statistically definitive as the anagen to telogen ratio data, the Nourishing Scalp Treatment caused a greater percentage reduction in the number of hairs lost and the number of bulbous hairs lost than did the placebo. (Table 3). Perhaps most importantly, the data show that the objective increases in scalp condition were easily perceived by the test subjects. At the end of the 90-day evaluation period more than 50% of test subjects perceived improvement in 9/11 of the subjective evaluation parameters. (Table 4). Further, a greater percentage of test subjects reported improvement with the Nourishing Scalp Treatment than for the placebo for 10/11 parameters. (Table 4). Additionally, average values for the subjective evaluations showed that the Nourishing Scalp Treatment caused a statistically significant improvement in hair loss in sink observed by test subjects, which was statistically significantly greater than the improvement observed by the placebo group. (Table 5). Also, although not as statistically definitive as the hair loss observed in sink data, the Nourishing Scalp Treatment also caused greater improvements in ease of dry combing, ease of wet combing, hair body when dry, and hair shine when dry than did the placebo. (Table 5). Hair body and shine are particularly important parameters of hair appearance.

The results discussed above clearly demonstrate that even using just the scalp treatment of Example 1 optimizes scalp health and induces increased visual and tactile hair quality.

TABLE 3

Average Results of the Objectively Measured Parameters[a]

| Parameter Evaluated | Placebo Nourishing Scalp Treatment | | | Active Nourishing Scalp Treatment | | |
|---|---|---|---|---|---|---|
| | Initial | Day 45 | Day 90 | Initial | Day 45 | Day 90 |
| Total Weight of Hair Lost | 0.0593 | 0.0182 | 0.0100 | 0.0550 | 0.0220 | 0.0094 |
| Percentage Reduction[b] | — | 58.90 | 73.47 | — | 43.86 | 70.12 |
| Number of Hairs Lost | 45.53 | 25.40 | 14.70 | 77.76 | 47.56 | 30.32 |
| Percentage Reduction[b] | — | 18.70 | 45.44 | — | 35.00 | 51.81 |
| Number of Bulbous Hairs Lost | 50.10 | 16.73 | 9.07 | 48.94 | 17.53 | 10.12 |
| Percentage Reduction[b] | — | 56.59 | 72.14 | — | 54.93 | 74.31 |
| Weight of Bulbous Hair Lost | 0.0459 | 0.0136 | 0.0072 | 0.0434 | 0.0151 | 0.0072 |
| Percentage Reduction[b] | — | 58.96 | 75.06 | — | 40.50 | 62.37 |
| Anagen-Telogen Ratio | 2.95 | 4.67 | 4.00 | 3.04 | 3.57 | 5.00 |
| Percentage Increase[c] | — | 48.32 | 35.43 | — | 17.33 | 64.56 |
| Percentage Difference[d] in Hair Diameter | — | 4.94 | 9.12 | — | 3.33 | 7.66 |
| Cross-Sectional Area | — | 0.11 | 0.21 | — | 0.07 | 0.17 |
| Circumference | — | 0.05 | 0.09 | — | 0.03 | 0.08 |

[a]Values listed in bold type were found to be statistically significantly different from initial (Day 0) values at the 95% confidence level using the student t-test.
[b]The percentage reduction is calculated by subtracting the initial value from the value at the evaluation point and then dividing this value by the initial value.
[c]The percentage increase is calculated by subtracting the initial value from the value at the evaluation point and then dividing this value by the initial value.
[d]The percentage difference is calculated by subtracting the initial value from the value at the evaluation point and then dividing this value by the initial value.

TABLE 4

Test Subjects' Perception of the Improvement of the Hair Based Upon the Subjective Questionnaire Results

| Parameter Evaluated | Percentage of Subjects Reporting Improvement[a] | |
|---|---|---|
| | Placebo NST Results | Active NST Results |
| Hair Loss Observed in Sink | 51.9 | 75.8 |
| Hair Loss When Dry Combing | 48.1 | 66.7 |
| Hair Breakage When Dry Combing | 48.1 | 66.7 |
| Hair Breakage When Wet Combing | 44.4 | 63.6 |
| Ease of Dry Combing | 51.9 | 54.5 |
| Ease of Wet Combing | 44.4 | 69.7 |
| Hair Manageability | 51.9 | 60.6 |
| Hair Volume When Dry | 33.3 | 24.2 |
| Hair Thickness When Dry | 25.9 | 30.3 |
| Hair Body When Dry | 44.4 | 51.5 |
| Hair Shine When Dry | 48.1 | 54.5 |

[a]Calculated by subtracting the Day 90 results from the initial (baseline) results and dividing by the initial (baseline) results.

TABLE 5

Average Results of Subjective Evaluations[a,b]

| Subjective Parameter | Placebo Nourishing Scalp Treatment | | | | Active Nourishing Scalp Treatment | | | |
|---|---|---|---|---|---|---|---|---|
| | Initial Results | | Day 90 Results | | Initial Results | | Day 90 Results | |
| | Average | Std Dev | Average | Std Dev | Average | Std Dev | Average | Std Dev |
| Hair Loss Observed in Sink | 2.82 | 0.83 | 3.44 | 0.64 | 2.58 | 0.94 | 3.52 | 0.83 |
| Hair Loss Observed When Dry Combing | 3.00 | 0.96 | 3.56 | 0.64 | 2.70 | 0.85 | 3.49 | 0.71 |
| Hair Breakage When Dry Combing | 3.15 | 0.95 | 3.74 | 0.71 | 2.76 | 0.83 | 3.52 | 0.87 |
| Hair Breakage When Wet Combing | 3.44 | 0.89 | 3.96 | 0.71 | 2.82 | 1.19 | 3.73 | 1.01 |
| Ease of Dry Combing | 3.15 | 0.77 | 3.70 | 0.91 | 2.97 | 1.13 | 3.73 | 0.98 |
| Ease of Wet Combing | 3.27 | 0.88 | 3.85 | 0.82 | 3.03 | 0.98 | 3.91 | 0.63 |
| Hair Manageability | 2.85 | 1.13 | 3.48 | 0.98 | 2.73 | 1.01 | 3.30 | 0.88 |
| Hair Volume When Dry | 2.82 | 0.83 | 3.04 | 0.94 | 3.00 | 1.09 | 2.97 | 1.05 |
| Hair Thickness When Dry | 2.67 | 0.83 | 2.85 | 0.82 | 2.61 | 0.86 | 2.79 | 0.96 |

TABLE 5-continued

Average Results of Subjective Evaluations[a,b]

| Subjective Parameter | Placebo Nourishing Scalp Treatment | | | | Active Nourishing Scalp Treatment | | | |
|---|---|---|---|---|---|---|---|---|
| | Initial Results | | Day 90 Results | | Initial Results | | Day 90 Results | |
| | Average | Std Dev | Average | Std Dev | Average | Std Dev | Average | Std Dev |
| Hair Body When Dry | 2.82 | 0.74 | 3.04 | 0.98 | 2.61 | 1.00 | 3.06 | 1.14 |
| Hair Shine When Dry | 2.96 | 1.16 | 3.63 | 1.15 | 3.15 | 0.80 | 3.67 | 0.99 |

[a]Day 90 values listed in bold were statistically significantly different from the initial (Day 0) values using the Mann-Whitney test.
[b]For underlined Day 90 values, the difference between the values for the Nourishing Scalp Treatment and the placebo was statistically significantly different using the Mann-Whitney test.

It will be apparent that the precise details of the methods and compositions described may be varied or modified without departing from the spirit of the described invention. We claim all such modifications and variations that fall within the scope and spirit of the claims below.

We claim:

1. A hair care formulation that enhances visual and/or tactile qualities of hair comprising:
   0.00001–10% pyridoxine hydrochloride;
   0.0001–12% glycyrrhizinic acid;
   0.001–20% pantothenic acid;
   0.0001–7% pyrrolidone;
   0.0001–15% antimicrobial agent;
   0.0001–10% zinc; and
   0.00001–5% antioxidant.

2. The hair care formulation of claim 1, wherein the formulation comprises about:
   0.1% pyridoxine hydrochloride;
   0.05% glycyrrhizinic acid;
   0.125 pantothenic acid;
   0.01% pyrrolidone;
   0.05% antimicrobial agent;
   0.01% zinc; and
   0.01% antioxidant.

3. The hair care formulation of claim 1, where in the glycyrrhizinic acid comprises one or more of monoammonium glycyrrhezinate or dipotassium glycyrrhezinate.

4. The hair care formulation of claim 1, wherein the pantothenic acid comprises panthenol.

5. The hair care formulation of claim 1, wherein the pyrrolidone comprises pyrrolidone carboxylic acid.

6. The hair care formulation of claim 1, wherein the antimicrobial agent comprises one or more of cajuput oil, lemongrass, lavender, or tea tree oil.

7. The hair care formulation of claim 6, wherein the antimicrobial agent comprises tea tree oil.

8. The hair care formulation of claim 1, wherein the zinc comprises a zinc containing compound.

9. The hair care formulation of claim 8, wherein the zinc containing compound comprises a zinc pyrrolidone.

10. The hair care formulation of claim 9, wherein the zinc pyrrolidone comprises zinc pyrrolidone carboxylic acid.

11. The hair care formulation of claim 1, wherein the antioxidant comprises one or more of green tea extract and superoxide dismutase.

12. The hair care formulation of claim 1, further comprising a blood flow stimulator.

13. The hair care formulation of claim 12, wherein the blood flow stimulator comprises one or more of zingiber officinale root oil, zingiber officinale extract, or menthol.

14. The hair care formulation of claim 1, further comprising a moisturizer.

15. The hair care formulation of claim 1, wherein the formulation comprises about:
   0.00001–10% pyridoxine hydrochloride;
   0.0001–12% dipotassium glycyrrhizinic acid;
   0.001–20% panthenol;
   0.0001–10% zinc pyrrolidone carboxylic acid;
   0.0001–15% tea tree leaf oil;
   0.0001–10% zinc; and
   0.00001–5% green tree extract or superoxide dismutase.

16. The hair care formulation of claim 15, comprising about:
   0.1% pyridoxine hydrochloride;
   0.05% dipotassium glycyrrhizinic acid;
   0.125% panthenol;
   0.1% zinc pyrrolidone carboxylic acid;
   0.05% tea tree leaf oil;
   0.1% zinc; and
   0.1% green tree extract or superoxide dismutase.

17. The hair care formulation of claim 15, wherein the hair care formulation is included in a separate shampoo formulation and conditioner formulation.

18. The hair care formulation of claim 17, wherein the hair care formulation is also included in a separate scalp treatment formulation, which is not a shampoo formulation or conditioner formulation.

19. The hair care formulation of claim 17, wherein the hair care formulation is also included in a separate revitalizing conditioner formulation.

20. The hair care formulation of claim 15, wherein the hair care formulation is included in a separate shampoo formulation, conditioner formulation, revitalizing conditioner formulation, and scalp treatment formulation.

21. The hair care formulation of claim 17, wherein the shampoo and conditioner formulations comprise a set of two shampoos and two conditioners.

22. The hair care formulation of claim 1, wherein the hair care formulation is a scalp treatment formulation comprising about:

| Ingredient | Percentage by Weight (w/w) |
|---|---|
| Water | 90.2200 |
| SD Alcohol 40-B | 5.0000 |
| Isoceteth-20 | 1.5000 |

-continued

| Ingredient | Percentage by Weight (w/w) |
|---|---|
| Benzyl Alcohol | 0.4500 |
| Water and Butylene Glycol and *Serenoa Serrulata* (Saw Palmetto) Fruit Extract | 0.2500 |
| Water and Butylene Glycol and *Panax Ginseng* Root Extract | 0.2500 |
| Panthenol (Liquid 50%) | 0.2500 |
| Water and Butylene Glycol and *Swertia Japonica* Extract | 0.2500 |
| Water and Butylene Glycol and *Zingiber Officinale* (Ginger) Root Extract | 0.2500 |
| Sodium Benzoate | 0.3000 |
| Methylparaben | 0.2000 |
| Polysorbate 80 | 0.1500 |
| Zinc PCA | 0.1000 |
| Galactoarabinan | 0.1000 |
| Tocopheryl Acetate | 0.1000 |
| Pyridoxine HCl | 0.1000 |
| Propylparaben | 0.1000 |
| Disodium EDTA | 0.1000 |
| Menthol | 0.0500 |
| *Melaleuca Alternifolia* (Tea Tree) Leaf Oil | 0.0500 |
| Dipotassium Glycyrrhizate | 0.0500 |
| *Camellia Sinensis* Leaf Extract | 0.0500 |
| Superoxide Dismutase | 0.0100 |
| *Zingiber Officinale* (Ginger) Root Oil | 0.0500 |
| Butylparaben | 0.0500 |
| Ubiquinone (Coenzyme Q-10) | 0.0100 |
| Retinyl Palmitate | 0.0100 |
| Total | 100.0000 |

23. The hair care formulation of claim 1, wherein the hair care formulation is a daily shampoo formulation or deep cleansing shampoo formulation comprising about:

| Ingredient | Percentage by Weight (w/w) | |
|---|---|---|
| | Daily Shampoo | Deep Cleansing Shampoo |
| Sodium Lauryl Sulfoacetate and Disodium Laureth Sulfosuccinate | 26.00000 | — |
| Ammonium Laureth Sulfate | 21.50000 | 18.30000 |
| Water | 27.12222 | 43.83222 |
| Decyl Glucoside | — | 18.30000 |
| Cocamidopropyl Betaine | 14.50000 | 15.25000 |
| Coco-Glucoside and Glyceryl Oleate | 4.50000 | — |
| PEG-120 Methyl Glucose Dioleate | — | 2.00000 |
| Butylene Glycol | 1.75000 | — |
| Sodium Coco PG-Dimonium Chloride Phosphate | 0.50000 | 0.50000 |
| Triethanolamine 99% | 0.80000 | 0.42000 |
| Sodium Benzoate | 0.40000 | 0.40000 |
| Fragrance | 0.40000 | 0.35000 |
| Citric Acid | — | 0.12000 |
| Capryloyl Glycine | 0.20000 | 0.20000 |
| Undecylenoyl Glycine | 0.10000 | 0.10000 |
| Polysorbate 80 | 0.00722 | 0.00722 |
| Stearyldimonium Hydroxypropyl Hydrolyzed Wheat Protein | 1.00000 | — |
| Wheat Amino Acids | 1.00000 | — |
| Phytantriol | 0.10000 | 0.10000 |
| Panthenol (50% liquid) | 0.10000 | 0.10000 |
| Water and Butylene Glycol and *Swertia Japonica* Extract | 0.00722 | 0.00722 |
| Butylene Glycol and *Panax Ginseng* Root Extract | 0.00361 | 0.00361 |
| Butylene Glycol and *Serenoa Serrulata* Extract | 0.00361 | 0.00361 |
| Pyridoxine Hydrochloride (Vitamin B6) | 0.00144 | 0.00144 |
| Zinc PCA | 0.00144 | 0.00144 |

-continued

| Ingredient | Percentage by Weight (w/w) | |
|---|---|---|
| | Daily Shampoo | Deep Cleansing Shampoo |
| Superoxide Dismutase | 0.00108 | 0.00108 |
| *Camellia Sinensis* Leaf Extract (Green Tea Extract) | 0.00072 | 0.00072 |
| Dipotassium Glycyrrhizate | 0.00072 | 0.00072 |
| *Melaleuca Alternifolia* (Tea Tree) Leaf Oil | 0.00072 | 0.00072 |
| Total | 100.00000 | 100.00000 |

24. The hair care formulation of claim 1, wherein the hair care formulation is a light conditioner formulation or revitalizing conditioner formulation comprising about:

| Ingredient | Percentage by Weight (w/w) | |
|---|---|---|
| | Light Conditioner | Revitalizing Conditioner |
| Water | 79.77222 | 76.24222 |
| Glyceryl Stearate (and) PEG-100 Stearate | 3.50000 | — |
| C14–22 Alkylalcohol and C12–20 Alkylglucoside | 2.50000 | 3.00000 |
| Behentrimonium Chloride | — | 2.50000 |
| Cyclomethicone | 2.00000 | 1.50000 |
| Quaternium-82 | 2.00000 | — |
| Cetyl Alcohol | 1.50000 | 2.50000 |
| Wheat Germamidopropyl Dimonium Hydroxypropyl Hydrolyzed Wheat Protein | — | 3.00000 |
| Glyceryl Stearate and PEG-100 Stearate | — | 1.50000 |
| Trilaureth-4 Phosphate | — | 1.50000 |
| Stearyl Alcohol | 1.20000 | 1.00000 |
| Glyceryl Stearate | 1.00000 | — |
| Benzyl Alcohol | 0.95000 | 0.95000 |
| Hydroxyethylcellulose | 0.75000 | 1.00000 |
| Sodium Coco PG-Dimonium Chloride Phosphate | 0.50000 | 0.50000 |
| Stearamidopropyl Dimethylamine | — | 0.50000 |
| Citric Acid | 0.45000 | 0.28000 |
| Fragrance | 0.40000 | 0.40000 |
| Stearamidopropyl Dimethylamine | 0.40000 | 0.50000 |
| Hydrogenated Vegetable Oil | 0.25000 | — |
| Phenyl Trimethicone | 0.25000 | — |
| Methylparaben | 0.20000 | 0.20000 |
| Sodium Benzoate | 0.20000 | 0.20000 |
| Disodium EDTA | 0.10000 | 0.10000 |
| Propylparaben | 0.10000 | 0.10000 |
| Butylparaben | 0.05000 | 0.05000 |
| Polysorbate 80 | 0.00722 | 0.00722 |
| Stearyldimonium Hydroxypropyl Hydrolyzed Wheat Protein | 0.50000 | — |
| Wheat Amino Acids | 0.50000 | 1.00000 |
| Cinnamidopropyltrimonium Chloride | 0.50000 | 0.50000 |
| Phytantriol | 0.10000 | 0.10000 |
| Panthenol (50% Liquid) | 0.10000 | — |
| Galactoarabinan | 0.20000 | 0.20000 |
| Sodium Cocoyl Amino Acids and Potassium Dimethyl Copolyol Panthenyl Phosphate | — | 0.10000 |
| Butylene Glycol and *Helianthus Annuus* (Sunflower) Seed Extract | — | 0.05000 |
| Water and Butylene Glycol and *Swertia Japonica* Extract | 0.00722 | 0.00722 |
| Butylene Glycol and *Panax Ginseng* Root Extract | 0.00361 | 0.00361 |
| Butylene Glycol and *Serenoa Serrulata* Extract | 0.00361 | 0.00361 |
| Pyridoxine Hydrochloride (Vitamin B6) | 0.00144 | 0.00144 |
| Zinc PCA | 0.00144 | 0.00144 |

| Ingredient | Percentage by Weight (w/w) | |
|---|---|---|
| | Light Conditioner | Revitalizing Conditioner |
| Superoxide Dismutase | 0.00108 | 0.00108 |
| *Camellia Sinensis* Leaf Extract (Green Tea Extract) | 0.00072 | 0.00072 |
| Dipotassium Glycyrrhizate | 0.00072 | 0.00072 |
| *Melaleuca Alternifolia* (Tea Tree) Leaf Oil | 0.00072 | 0.00072 |
| Total | 100.00000 | 100.00000. |

25. A set of hair care formulations, comprising first and second shampoo formulations, first and second conditioner formulations, and a scalp treatment formulation, wherein the scalp treatment formulation comprises about:

| Ingredient | Percentage by Weight (w/w) |
|---|---|
| Water | 90.2200 |
| SD Alcohol 40-B | 5.0000 |
| Isoceteth-20 | 1.5000 |
| Benzyl Alcohol | 0.4500 |
| Water and Butylene Glycol and *Serenoa Serrulata* (Saw Palmetto) Fruit Extract | 0.2500 |
| Water and Butylene Glycol and Panax Ginseng Root Extract | 0.2500 |
| Panthenol (Liquid 50%) | 0.2500 |
| Water and Butylene Glycol and *Swertia Japonica* Extract | 0.2500 |
| Water and Butylene Glycol and *Zingiber Officinale* (Ginger) Root Extract | 0.2500 |
| Sodium Benzoate | 0.3000 |
| Methylparaben | 0.2000 |
| Polysorbate 80 | 0.1500 |
| Zinc PCA | 0.1000 |
| Galactoarabinan | 0.1000 |
| Tocopheryl Acetate | 0.1000 |
| Pyridoxine HCl | 0.1000 |
| Propylparaben | 0.1000 |
| Disodium EDTA | 0.1000 |
| Menthol | 0.0500 |
| *Melaleuca Alternifolia* (Tea Tree) Leaf Oil | 0.0500 |
| Dipotassium Glycyrrhizate | 0.0500 |
| *Camellia Sinensis* Leaf Extract | 0.0500 |
| Superoxide Dismutase | 0.0100 |
| *Zingiber Officinale* (Ginger) Root Oil | 0.0500 |
| Butylparaben | 0.0500 |
| Ubiquinone (Coenzyme Q-10) | 0.0100 |
| Retinyl Palmitate | 0.0100 |
| Total | 100.0000 | the first shampoo formulation is a daily shampoo formulation and the second shampoo formulation is a deep cleansing shampoo formulation, wherein the daily shampoo formulation and deep cleansing formulation comprise about:

| Ingredient | Percentage by Weight (w/w) | |
|---|---|---|
| | Daily Shampoo | Deep Cleansing Shampoo |
| Sodium Lauryl Sulfoacetate and Disodium Laureth Sulfosuccinate | 26.00000 | — |
| Ammonium Laureth Sulfate | 21.50000 | 18.30000 |
| Water | 27.12222 | 43.83222 |
| Decyl Glucoside | — | 18.30000 |
| Cocamidopropyl Betaine | 14.50000 | 15.25000 |
| Coco-Glucoside and Glyceryl Oleate | 4.50000 | — |
| PEG-120 Methyl Glucose Dioleate | — | 2.00000 |
| Butylene Glycol | 1.75000 | — |
| Sodium Coco PG-Dimonium Chloride Phosphate | 0.50000 | 0.50000 |
| Triethanolamine 99% | 0.80000 | 0.42000 |
| Sodium Benzoate | 0.40000 | 0.40000 |
| Fragrance | 0.40000 | 0.35000 |
| Citric Acid | — | 0.12000 |
| Capryloyl Glycine | 0.20000 | 0.20000 |
| Undecylenoyl Glycine | 0.10000 | 0.10000 |
| Polysorbate 80 | 0.00722 | 0.00722 |
| Stearyldimonium Hydroxypropyl Hydrolyzed Wheat Protein | 1.00000 | — |
| Wheat Amino Acids | 1.00000 | — |
| Phytantriol | 0.10000 | 0.10000 |
| Panthenol (50% liquid) | 0.10000 | 0.10000 |
| Water and Butylene Glycol and *Swertia Japonica* Extract | 0.00722 | 0.00722 |
| Butylene Glycol and Panax Ginseng Root Extract | 0.00361 | 0.00361 |
| Butylene Glycol and *Serenoa Serrulata* Extract | 0.00361 | 0.00361 |
| Pyridoxine Hydrochloride (Vitamin B6) | 0.00144 | 0.00144 |
| Zinc PCA | 0.00144 | 0.00144 |
| Superoxide Dismutase | 0.00108 | 0.00108 |
| *Camellia Sinensis* Leaf Extract (Green Tea Extract) | 0.00072 | 0.00072 |
| Dipotassium Glycyrrhizate | 0.00072 | 0.00072 |
| *Melaleuca Alternifolia* (Tea Tree) Leaf Oil | 0.00072 | 0.00072 |
| Total | 100.00000 | 100.00000 | the first conditioner formulation is a light conditioner and the second conditioner formulation is a revitalizing conditioner formulation, wherein the first and second conditioner formulations comprise about:

| Ingredient | Percentage by Weight (w/w) | |
|---|---|---|
| | Light Conditioner | Revitalizing Conditioner |
| Water | 79.77222 | 76.24222 |
| Glyceryl Stearate (and) PEG-100 Stearate | 3.50000 | — |
| C14–22 Alkylalcohol and C12–20 Alkylglucoside | 2.50000 | 3.00000 |
| Behentrimonium Chloride | — | 2.50000 |
| Cyclomethicone | 2.00000 | 1.50000 |
| Quaternium-82 | 2.00000 | — |
| Cetyl Alcohol | 1.50000 | 2.50000 |
| Wheat Germamidopropyl Dimonium Hydroxypropyl Hydrolyzed Wheat Protein | — | 3.00000 |
| Glyceryl Stearate and PEG-100 Stearate | — | 1.50000 |
| Trilaureth-4 Phosphate | — | 1.50000 |
| Stearyl Alcohol | 1.20000 | 1.00000 |
| Glyceryl Stearate | 1.00000 | — |
| Benzyl Alcohol | 0.95000 | 0.95000 |
| Hydroxyethylcellulose | 0.75000 | 1.00000 |
| Sodium Coco PG-Dimonium Chloride Phosphate | 0.50000 | 0.50000 |
| Stearamidopropyl Dimethylamine | — | 0.50000 |

-continued

| Ingredient | Percentage by Weight (w/w) | |
|---|---|---|
| | Light Conditioner | Revitalizing Conditioner |
| Citric Acid | 0.45000 | 0.28000 |
| Fragrance | 0.40000 | 0.40000 |
| Stearamidopropyl Dimethylamine | 0.40000 | 0.50000 |
| Hydrogenated Vegetable Oil | 0.25000 | — |
| Phenyl Trimethicone | 0.25000 | — |
| Methylparaben | 0.20000 | 0.20000 |
| Sodium Benzoate | 0.20000 | 0.20000 |
| Disodium EDTA | 0.10000 | 0.10000 |
| Propylparaben | 0.10000 | 0.10000 |
| Butylparaben | 0.05000 | 0.05000 |
| Polysorbate 80 | 0.00722 | 0.00722 |
| Stearyldimonium Hydroxypropyl Hydrolyzed Wheat Protein | 0.50000 | — |
| Wheat Amino Acids | 0.50000 | 1.00000 |
| Cinnamidopropyltrimonium Chloride | 0.50000 | 0.50000 |
| Phytantriol | 0.10000 | 0.10000 |
| Panthenol (50% Liquid) | 0.10000 | — |
| Galactoarabinan | 0.20000 | 0.20000 |
| Sodium Cocoyl Amino Acids and Potassium Dimethyl Copolyol Panthenyl Phosphate | — | 0.10000 |
| Butylene Glycol and *Helianthus Annuus* (Sunflower) Seed Extract | — | 0.05000 |
| Water and Butylene Glycol and *Swertia Japonica* Extract | 0.00722 | 0.00722 |
| Butylene Glycol and Panax Ginseng Root Extract | 0.00361 | 0.00361 |
| Butylene Glycol and *Serenoa Serrulata* Extract | 0.00361 | 0.00361 |
| Pyridoxine Hydrochloride (Vitamin B6) | 0.00144 | 0.00144 |
| Zinc PCA | 0.00144 | 0.00144 |
| Superoxide Dismutase | 0.00108 | 0.00108 |
| *Camellia Sinensis* Leaf Extract (Green Tea Extract) | 0.00072 | 0.00072 |
| Dipotassium Glycyrrhizate | 0.00072 | 0.00072 |
| *Melaleuca Alternifolia* (Tea Tree) Leaf Oil | 0.00072 | 0.00072 |
| Total | 100.00000 | 100.00000. |

26. A method of enhancing an appearance and/or texture of hair, comprising applying the hair care formulation of claim 1 to the hair.

27. A method of enhancing an appearance and/or texture of hair comprising applying the hair care formulation of claim 15 to the hair.

28. The method of claim 27, wherein the hair care formulation is included in a separate shampoo formulation and conditioner formulation, and the shampoo formulation is applied to the hair to cleanse it, and the conditioner formulation is applied to the hair to condition it.

29. The method of claim 27 wherein the hair care formulation is included in a separate shampoo formulation, deep cleansing shampoo formulation, conditioner formulation, revitalizing conditioner formulation, and scalp treatment formulation, wherein:

the deep cleansing shampoo formulation is applied to the hair 1–2 times per week, and the daily shampoo is applied the other days of the week;

the revitalizing conditioner formulation is applied 1–2 times per week, and the light conditioner formulation is applied to the hair the other days of the week; and the scalp treatment formulation is applied to the scalp each day of the week.

30. The method of claim 29, wherein the scalp treatment formulation comprises about:

| Ingredient | Percentage by Weight (w/w) |
|---|---|
| Water | 90.2200 |
| SD Alcohol 40-B | 5.0000 |
| Isoceteth-20 | 1.5000 |
| Benzyl Alcohol | 0.4500 |
| Water and Butylene Glycol and *Serenoa Serrulata* (Saw Palmetto) Fruit Extract | 0.2500 |
| Water and Butylene Glycol and Panax Ginseng Root Extract | 0.2500 |
| Panthenol (Liquid 50%) | 0.2500 |
| Water and Butylene Glycol and *Swertia Japonica* Extract | 0.2500 |
| Water and Butylene Glycol and *Zingiber Officinale* (Ginger) Root Extract | 0.2500 |
| Sodium Benzoate | 0.3000 |
| Methylparaben | 0.2000 |
| Polysorbate 80 | 0.1500 |
| Zinc PCA | 0.1000 |
| Galactoarabinan | 0.1000 |
| Tocopheryl Acetate | 0.1000 |
| Pyridoxine HCl | 0.1000 |
| Propylparaben | 0.1000 |
| Disodium EDTA | 0.1000 |
| Menthol | 0.0500 |
| *Melaleuca Alternifolia* (Tea Tree) Leaf Oil | 0.0500 |
| Dipotassium Glycyrrhizate | 0.0500 |
| *Camellia Sinensis* Leaf Extract | 0.0500 |
| Superoxide Dismutase | 0.0100 |
| *Zingiber Officinale* (Ginger) Root Oil | 0.0500 |
| Butylparaben | 0.0500 |
| Ubiquinone (Coenzyme Q-10) | 0.0100 |
| Retinyl Palmitate | 0.0100 |
| Total | 100.0000. |

31. The method of claim 29, wherein the daily shampoo formulation and deep cleansing formulation comprise about:

| Ingredient | Percentage by Weight (w/w) | |
|---|---|---|
| | Daily Shampoo | Deep Cleansing Shampoo |
| Sodium Lauryl Sulfoacetate and Disodium Laureth Sulfosuccinate | 26.00000 | — |
| Ammonium Laureth Sulfate | 21.50000 | 18.30000 |
| Water | 27.12222 | 43.83222 |
| Decyl Glucoside | — | 18.30000 |
| Cocamidopropyl Betaine | 14.50000 | 15.25000 |
| Coco-Glucoside and Glyceryl Oleate | 4.50000 | — |
| PEG-120 Methyl Glucose Dioleate | — | 2.00000 |
| Butylene Glycol | 1.75000 | — |
| Sodium Coco PG-Dimonium Chloride Phosphate | 0.50000 | 0.50000 |
| Triethanolamine 99% | 0.80000 | 0.42000 |
| Sodium Benzoate | 0.40000 | 0.40000 |
| Fragrance | 0.40000 | 0.35000 |
| Citric Acid | — | 0.12000 |
| Capryloyl Glycine | 0.20000 | 0.20000 |
| Undecylenoyl Glycine | 0.10000 | 0.10000 |
| Polysorbate 80 | 0.00722 | 0.00722 |
| Stearyldimonium Hydroxypropyl Hydrolyzed Wheat Protein | 1.00000 | — |
| Wheat Amino Acids | 1.00000 | — |
| Phytantriol | 0.10000 | 0.10000 |
| Panthenol (50% liquid) | 0.10000 | 0.10000 |
| Water and Butylene Glycol and *Swertia Japonica* Extract | 0.00722 | 0.00722 |
| Butylene Glycol and Panax Ginseng Root Extract | 0.00361 | 0.00361 |

-continued

| Ingredient | Percentage by Weight (w/w) | |
|---|---|---|
| | Daily Shampoo | Deep Cleansing Shampoo |
| Butylene Glycol and *Serenoa Serrulata* Extract | 0.00361 | 0.00361 |
| Pyridoxine Hydrochloride (Vitamin B6) | 0.00144 | 0.00144 |
| Zinc PCA | 0.00144 | 0.00144 |
| Superoxide Dismutase | 0.00108 | 0.00108 |
| *Camellia Sinensis* Leaf Extract (Green Tea Extract) | 0.00072 | 0.00072 |
| Dipotassium Glycyrrhizate | 0.00072 | 0.00072 |
| *Melaleuca Alternifolia* (Tea Tree) Leaf Oil | 0.00072 | 0.00072 |
| Total | 100.00000 | 100.00000. |

32. The method of claim 29, wherein the revitalizing conditioner formulation and light conditioner formulation comprise about:

| Ingredient | Percentage by Weight (w/w) | |
|---|---|---|
| | Light Conditioner | Revitalizing Conditioner |
| Water | 79.77222 | 76.24222 |
| Glyceryl Stearate (and) PEG-100 Stearate | 3.50000 | — |
| C14–22 Alkylalcohol and C12–20 Alkylglucoside | 2.50000 | 3.00000 |
| Behentrimonium Chloride | — | 2.50000 |
| Cyclomethicone | 2.00000 | 1.50000 |
| Quaternium-82 | 2.00000 | — |
| Cetyl Alcohol | 1.50000 | 2.50000 |
| Wheat Germamidopropyl Dimonium Hydroxypropyl Hydrolyzed Wheat Protein | — | 3.00000 |
| Glyceryl Stearate and PEG-100 Stearate | — | 1.50000 |
| Trilaureth-4 Phosphate | — | 1.50000 |
| Stearyl Alcohol | 1.20000 | 1.00000 |
| Glyceryl Stearate | 1.00000 | — |
| Benzyl Alcohol | 0.95000 | 0.95000 |
| Hydroxyethylcellulose | 0.75000 | 1.00000 |
| Sodium Coco PG-Dimonium Chloride Phosphate | 0.50000 | 0.50000 |
| Stearamidopropyl Dimethylamine | — | 0.50000 |
| Citric Acid | 0.45000 | 0.28000 |
| Fragrance | 0.40000 | 0.40000 |
| Stearamidopropyl Dimethylamine | 0.40000 | 0.50000 |
| Hydrogenated Vegetable Oil | 0.25000 | — |
| Phenyl Trimethicone | 0.25000 | — |
| Methylparaben | 0.20000 | 0.20000 |
| Sodium Benzoate | 0.20000 | 0.20000 |
| Disodium EDTA | 0.10000 | 0.10000 |
| Propylparaben | 0.10000 | 0.10000 |
| Butylparaben | 0.05000 | 0.05000 |
| Polysorbate 80 | 0.00722 | 0.00722 |
| Stearyldimonium Hydroxypropyl Hydrolyzed Wheat Protein | 0.50000 | — |
| Wheat Amino Acids | 0.50000 | 1.00000 |
| Cinnamidopropyltrimonium Chloride | 0.50000 | 0.50000 |
| Phytantriol | 0.10000 | 0.10000 |
| Panthenol (50% Liquid) | 0.10000 | — |
| Galactoarabinan | 0.20000 | 0.20000 |
| Sodium Cocoyl Amino Acids and Potassium Dimethyl Copolyol Panthenyl Phosphate | — | 0.10000 |
| Butylene Glycol and *Helianthus Annuus* (Sunflower) Seed Extract | — | 0.05000 |
| Water and Butylene Glycol and *Swertia Japonica* Extract | 0.00722 | 0.00722 |
| Butylene Glycol and *Panax Ginseng* Root Extract | 0.00361 | 0.00361 |

-continued

| Ingredient | Percentage by Weight (w/w) | |
|---|---|---|
| | Light Conditioner | Revitalizing Conditioner |
| Butylene Glycol and *Serenoa Serrulata* Extract | 0.00361 | 0.00361 |
| Pyridoxine Hydrochloride (Vitamin B6) | 0.00144 | 0.00144 |
| Zinc PCA | 0.00144 | 0.00144 |
| Superoxide Dismutase | 0.00108 | 0.00108 |
| *Camellia Sinensis* Leaf Extract (Green Tea Extract) | 0.00072 | 0.00072 |
| Dipotassium Glycyrrhizate | 0.00072 | 0.00072 |
| *Melaleuca Alternifolia* (Tea Tree) Leaf Oil | 0.00072 | 0.00072 |
| Total | 100.00000 | 100.00000. |

33. A kit, comprising a shampoo and conditioner each of which comprise the formulation of claim 1.

34. The kit of claim 33, further comprising a scalp treatment formulation.

35. The kit of claim 33, wherein the shampoo comprises a regular shampoo and a deep cleansing shampoo.

36. The kit of claim 33, wherein the conditioner comprises a regular conditioner and a deep conditioner.

37. The kit of claim 33, further comprising instructions not to use another shampoo and conditioner.

38. The kit of claim 35, further comprising a scalp treatment formulation wherein the conditioner comprises a regular conditioner and a deep conditioner.

39. The method of claim 26, wherein the hair care formulation comprises about:

| Ingredient | Percentage by Weight (w/w) |
|---|---|
| Water | 90.2200 |
| SD Alcohol 40-B | 5.0000 |
| Isoceteth-20 | 1.5000 |
| Benzyl Alcohol | 0.4500 |
| Water and Butylene Glycol and *Serenoa Serrulata* (Saw Palmetto) Fruit Extract | 0.2500 |
| Water and Butylene Glycol and *Panax Ginseng* Root Extract | 0.2500 |
| Panthenol (Liquid 50%) | 0.2500 |
| Water and Butylene Glycol and *Swertia Japonica* Extract | 0.2500 |
| Water and Butylene Glycol and *Zingiber Officinale* (Ginger) Root Extract | 0.2500 |
| Sodium Benzoate | 0.3000 |
| Methylparaben | 0.2000 |
| Polysorbate 80 | 0.1500 |
| Zinc PCA | 0.1000 |
| Galactoarabinan | 0.1000 |
| Tocopheryl Acetate | 0.1000 |
| Pyridoxine HCl | 0.1000 |
| Propylparaben | 0.1000 |
| Disodium EDTA | 0.1000 |
| Menthol | 0.0500 |
| *Melaleuca Alternifolia* (Tea Tree) Leaf Oil | 0.0500 |
| Dipotassium Glycyrrhizate | 0.0500 |
| *Camellia Sinensis* Leaf Extract | 0.0500 |
| Superoxide Dismutase | 0.0100 |
| *Zingiber Officinale* (Ginger) Root Oil | 0.0500 |
| Butylparaben | 0.0500 |
| Ubiquinone (Coenzyme Q-10) | 0.0100 |
| Retinyl Palmitate | 0.0100 |
| Total | 100.0000. |

* * * * *